(12) United States Patent
Zhang et al.

(10) Patent No.: US 6,787,564 B2
(45) Date of Patent: Sep. 7, 2004

(54) OPTICALLY ACTIVE CLAUSENAMIDES, PROCESS OF THE PREPARATION THEREOF, PHARMACEUTICAL COMPOSITION CONTAINING THE SAME AND THEIR MEDICAL USE

(75) Inventors: Juntian Zhang, Beijing (CN); Liang Huang, Beijing (CN); Kemei Wu, Beijing (CN); Shiming Chen, Beijing (CN)

(73) Assignee: Institute of Materia Medica, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 10/108,233

(22) Filed: Mar. 26, 2002

(65) Prior Publication Data

US 2003/0207935 A1 Nov. 6, 2003

(51) Int. Cl.$^7$ .................. A61K 31/4015; C07D 207/26
(52) U.S. Cl. ......................... 514/424; 548/544
(58) Field of Search ........................... 514/424; 548/544

(56) References Cited

U.S. PATENT DOCUMENTS 4,751,315 A  *  6/1988  Hartwig et al. ............. 548/530
4,803,285 A  *  2/1989  Hartwig et al. ............. 548/551
4,879,390 A  * 11/1989  Chen et al. .................. 548/453

OTHER PUBLICATIONS

Acta Pharmaceutica Sinica 1997, 32(4): 259–263, Effects of (–), (+) Clausenamide On Central N–Methyl–D–Aspartate Receptors in Rodents, W.Z. zuan et al., English Language Abstract.

Acta Pharmaceutica Sinica 1998, 33(4), 296–299, "Metabolic Transformation of (–)– Clausenamide In Rat Liver Microsomes", Yao Qingqiany et al., English Language Abstract.

Acta Pharmacologica Sinica, 1999, 20(2), 112–116, "Effects of Naloxone on I–Clausenamide–Induced Long–Term Potentiation in Dentate Gyrus of Anesthetized Rats", LIU Shao–Lin et al.

* cited by examiner

Primary Examiner—Joseph K. McKane
Assistant Examiner—Kamal Saeed
(74) Attorney, Agent, or Firm—Darby & Darby

(57) ABSTRACT

The present invention relates to some new optically active clausenamide derivatives, process of the preparation thereof, a pharmaceutical composition containing the same and their medical use, particularly their use in the respects of hypoxia protective, nootropic and neurodegenerative disease such as cerebral ischemia, Alzheimer disease and vascular dementia.

6 Claims, 3 Drawing Sheets

OPTICALLY ACTIVE CLAUSENAMIDES, PROCESS OF THE PREPARATION THEREOF, PHARMACEUTICAL COMPOSITION CONTAINING THE SAME AND THEIR MEDICAL USE

FIELD OF THE INVENTION

The present invention relates to some new optically active clausenamide derivatives, process of the preparation thereof, a pharmaceutical composition containing the same and their medical use, particularly their use in the respects of hypoxia protective, nootropic and neurodegenerative disease such as cerebral ischemia, Alzheimer disease and vascular dementia.

BACKGROUND OF THE INVENTION

The average life span in Chinese population is now over 70 years of age.It increased by 100% as compared with before foundation of P.R. China. A scientific of study in abroad estimates that the proportion of the population over 65 years of age will increase to 18.8% by the 2025, when it will just exceed the proportion of children (18.6%). It means that one of 5 population in about 20 years later will be senile. Alzheimer's disease(AD) and vascular damentia(VD) refer to the presenile and senile form of the disease. i.e. under age 65 vs age 65 and over. Therefore, with the aging of population, the incidence of AD and VD will certainly be increased. The old men and their related neurodegenerative diseases especially various dementia have to undergoing two kinds of death, firstly the psychological death and then physical death. This is a heavy load for not only patients but also families and society. The aging of population is considered as a disadvantage factor, next to the war, pestilence, farming and shortage of resource and energy, to society's development and stability.

There are many drugs for prevention and treatment of senile dementia, such as cerebral vasodilators which can increase cognition function through improvement of blood flow and energy. However, a real valuable cerebral vasodilator should have high selectivity with no effect on brain metabolism and no "blood steal" phenomenon, it needs also to have antiplatelet aggregation and antithrombosis actions. Calcium channel blocker nimodipine accords with some demands as mentioned above, it acts on L-type but not the N- and T-type voltage dependent calcium channel. The drugs for central cholinergic system, the precoursor of acetyecholine(Ach) has weak therapeutic effect. Ach receptor agonists and cholinesterase inhibitors have certain sympmatically therapeutic effect, but its effect is short, and more important is that they can not affect athogenesis of dementia. Many neuropeptides and neurotrophine factors were considered as promising antidementia agents, but its clinical therapeutic effect is not good. The main reason for this is that these large molecules could not pass through the blood-brain barrier. Piracetam or 2-oxo-1 pyrolidine acetamide is usually considered as the prototype nootropic drug. In recent years, clinical studies indicated that the effect of piratcetam in improving memory impairment was mild or obscure. In addition, its mechanism of action is not fully understood, although it has been studied for nearly 30 years.

Racemic clausenamide was isolated from the aqueous extract of leaves of Rutoceae Clausena lausium(Lour) Skeels and had been claimed to have pronounced cerebral hypoxia protective and antiamnestic effect. Its potential medical use and processes of preparation from the plant had been granted a patent right for Chinese Academy of Medical Sciences and Bayer AG(EU patent No. 072514, U.S. Pat. No. 4,879,391 and Chinese patent No. 90107309). Methods for chemical synthesis of racemic clausenamide also had been applied for patent protection (German patent No. 3927370, EP No. 0414120).

SUMMARY OF THE INVENTION

The object of the present invention is to provide a new compound for the prevention and/or treatment of neurodegenerative disease such as cerebral ischemia, Alzheimer disease and vascular dementia.

Levoclausenamide as one of the active enantiomer of the racemic clausenamide is generally believed that an optically active clausenamide is the double of that of racemic clausenamide in respect to a biological activity or no any activity. The present inventors have now unexpectedly found that the biological activity of Levoclausenamides is significantly stronger than double of that of racemic clausenmide and is at 5–10 times more potent than that of racemic clausenamide in respect of said activity.

Furthermore, in both behavioral and electrophysiological studies. Levoclausen amide showed to facilitate learning and memory and increase neuronal plasticity. Besides,(−) clausenamide could antagonize Aβ induced neurotoxicity, inhibit neuron's apoptosis and tau protein over phosphorerytion, and therefore (−) clausenamide may be used as drug for prevention and/or treatment of dementia in early stage. The nootropic and antidementia tests of (−) clausenamide have been carried out in biochemical, molecular biological and morphological fields. For example, (−) clausenamide has been indicated to increase synapses of dentate gyrus in adult rats.

The present invention is directed to a new pharmacologically active chiral compound a substituted δ-butyrolactan (hereinafter called as levoclausenamide or (−) clausenamide) with the absolute configuration of 3S4R5R6S with levo rotation as shown in formula 1.

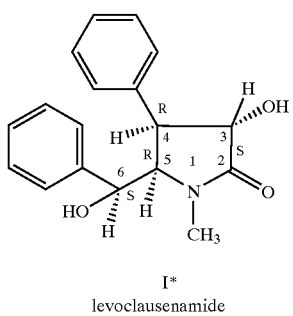

Formula 1

I*
levoclausenamide

The present invention provides to some new optically active stereoisomeric clausenamide derivatives of formula II,

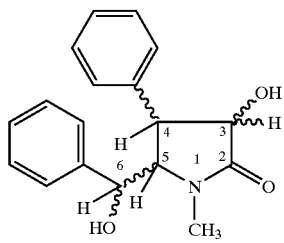

wherein said optically active clausenamide derivatives of formula II is selected from one of the following compound:

*3S4R5R6R (−)epiclausenamide,
*3R4S5S6S (+)epiclausenamide
**3S4R5S6R (−)neoclausenamide,
**3R4S5R6S (+)neoclausenamide
**3S4R5S6S(−)epineoclausenamide,
**3R4S5R6R(+)epineoclausen amide
*3S4S5S6R (+)cisclausenamide,
*3R4R5R6S (−)cisclausenamide
*3S4S5S6S (+)cisepiclausenamide,
*3R4R5R6R (−)cisepiclausenamide
*3S4S5R6S (−)cisneoclausenamide,
*3R4R5S6R (+)cisneoclausenamide
*3S4S5R6R(−)cisepineoclausenamide, and
*3R4R5S6S(+)cisepineoclausen-amide wherein "*" indicates new optically active clausenamide compounds;
    "**" indicates that racemic compounds of which is known but some biological activities thereof concerning noortropic, neurodegenerative disease have not been reported up to now.

The invention provides to some optically active clausenamide derivatives of formula I selected from one of the following compounds for the prevention and/or treatment of neurodegenerative diseases:

3S, 4R, 5R, 6S (−) Levoclausenamide,
3S4R5R6R (−) epiclausenamide,
3R4S5S6S (+)epiclausenamide,
3S4R5S6R (−)neoclausenamide,
3R4S5R6S (+)neoclausenamide,
3S4R5S6S(−)epineoclausenamide,
3R4S5R6R(+)epineoclausen amide,
3S4S5S6R (+)cisclausenamide,
3R4R5R6S (−)cisclausenamide,
3S4S5S6S (+)cisepiclausenamide,
3R4R5R6R (−)cisepiclausenamide,
3S4S5R6S (−)cisneoclausenamide,
3R4R5S6R (+)cisneoclausenamide,
3S4S5R6R(−)cisepineoclausenamide, and
3R4R5S6S(+)cisepineoclausen-amide.

The invention provides to a pharmaceutical composition comprising some optically active compounds of formula I and/or II and pharmaceutically carrier or excipient.

The invention provides to a pharmaceutical composition for the prevention and/or treatment of neurodegenerative diseases comprising any one of the optically active compounds of formula I and pharmaceutically carrier or excipient.

The invention provides to a use of any one of the optically active compounds of formula I and/or II for the manufacture of medicament for the prevention and/or treatment of neurodeganerative diseases.

The invention provides a method for the prevention and/or treatment of neurodegenerative disease comprising administrating to a patient suffered with neurodegenerative disease or high risk of neurodegenrative disease an effective prevention and/or treatment amount of any one of the optically active compounds of formula I and/or II.

The invention provides to a process for the preparation of levoclausenamide, which characterized in that:

1. De novo synthesis by using intramoleuclar inductive asymmetrical Dargen reaction to prepare compound (2*);

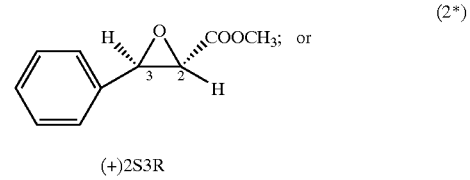

(+)2S3R

2. Biocatalystic resolution of said compound (2*); or
3. Chemical resolution of the racemic clausenamidone of formula (5*)

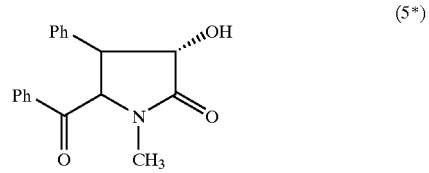

DETAILED DESCRIPTION OF THE INVENTION

The present invention provides an optically active Levoclausenamide of formula I Formula 1

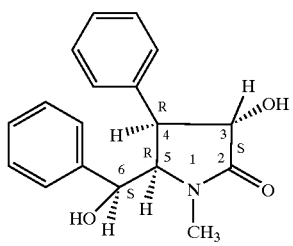

The present invention is directed to optically active clausenamide derivatives of formula I.

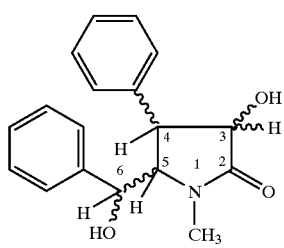

According to this invention, the compounds of formula I in the instant invention are one selected from the following specific compounds:

3S, 4R, 5R, 6S (−) Levoclausenamide,
3S4R5R6R (−) epiclausenamide,
3R4S5S6S (+)epiclausenamide
3S4R5S6R (−)neoclausenamide,
3R4S5R6S (+)neoclausenamide
3S4R5S6S(−)epineoclausenamide,
3R4S5R6R(+)epineoclausen amide
3S4S5S6R (+)cisclausenamide,
3R4R5R6S (−)cisclausenamide
3S4S5S6S (+)cisepiclausenamide,
3R4R5R6R (−)cisepiclausenamide
3S4S5R6S (−)cisneoclausenamide,
3R4R5S6R (+)cisneoclausenamide
3S4S5R6R(−)cisepineoclausenamide, and
3R4R5S6S(+)cisepineoclausen-amide.

The present invention also relates to a pharmaceutical composition comprising an optically active compound of formula I and/or II as an active ingredient and suitable pharmaceutically acceptable carrier or excipient. The an optically active compound of formula I and/or II are administrated alone or in the form of a pharmaceutical composition containing the same. Administration route may be intestinal or parenteral, such as oral, intramuscular, substcutaneous, transdermally, intransally, intraperitoneally, topically etc, said pharmaceutical preparations may formulated by mixing an optically active clausenamide derivatives of formula (I) with pharmaceutically acceptable diluents or excipients.

Furthermore, the pharmaceutical preparations may be various administration form such as a sterile isotonic aqueous solution, tablet, capsule, pill, drop and suppositories, paster, oilment, gel, pastes, cream, spray (including aerosols), lotion, suspensions, solution and emulsions of the active ingredient in aqueous or non-aqueous diluents, syrups, granules or powders.

The diluents to be used in pharmaceutical compositions (e.g. granulates) include customary pharmaceutically acceptable diluents or excipients such as starch, gelatine, silicic acid, polyethylene glycol. For liquid pharmaceutical preparation, a diluent or carrier may be water, alcohol, proplene glycol, vegetable oil, corn oil, peanut oil, olive oil, surface active agents, lubricants, disintegrating agents, preservative agent, flavoring agent or pigment.

According to the present invention, the term "patient" means to mammal, for example, human being.

The term "neurodegenerative disease" includes, for example, cerebral ischemia, Alzheimer disease and vascular dementia etc.

The levoclausenamide [(−)3S, 4R, 5R, 6S]] as one of some optically active clausenamide derivatives of the present invention may be prepared by the de novo asymmetric synthesis and the said detailed synthesis is shown in the following scheme 1.

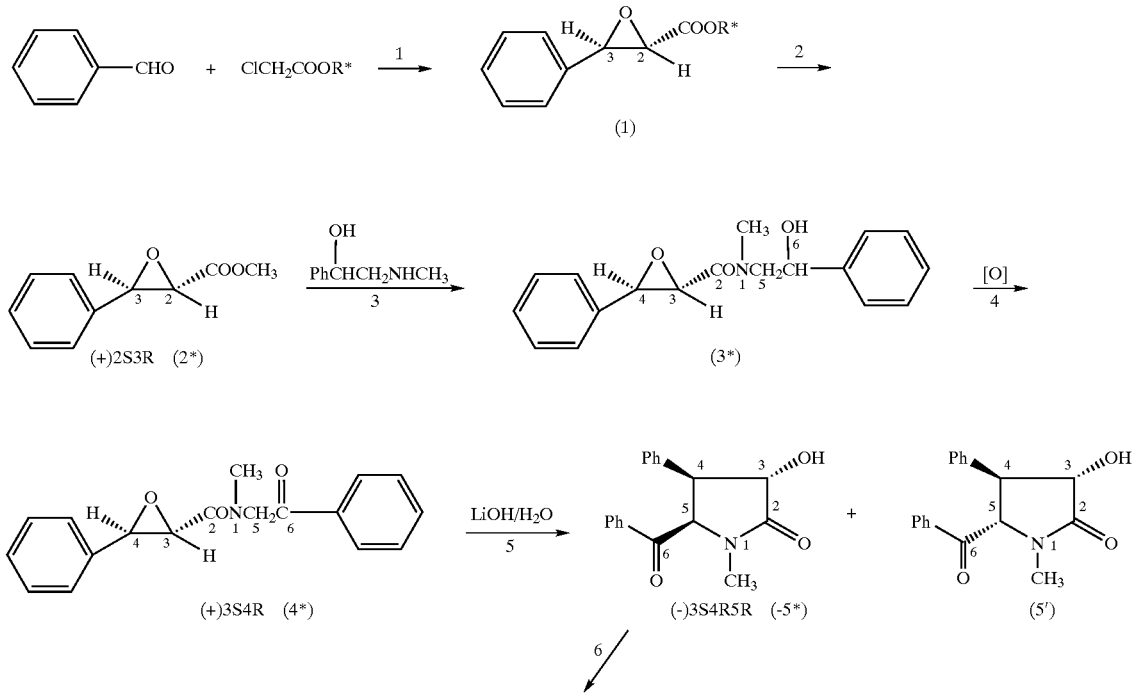

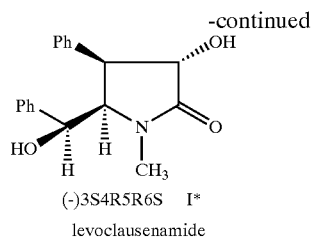

(-)3S4R5R6S I*
levoclausenamide

Scheme 1 consists of the following steps:

i) treating benzaldehyde with optical alkyl (R) chloroacetate in the presence of basic catalyst to give compound (1), the chiral group from natural or synthetic alcohol with appropriate configuration, preferably (+) menthol, (+) 8-phenylmenthol,(+) 8-β-naphthyl menthol, ii) adding sodium methoxide to a solution of compound (1) in methanol to yield compound(2*),(+)2S3R methyl 2,3 epoxy cinnamate, iii) interchanging easter group of compound(2*) with β-phenyl-ethanol-N-methyl amine in the presence of basic catalyst to yield compound (3*), 3S,4R-N-methyl-N-(β-hydroxyl-ethylbenzyl) 2,3 epoxy cinnamate compound(3*), or said compound (3*) is obtained directly with compound 1 by the procedure as described in (iii), iv) oxidizing compound 3 with potasssium permanganate and cuppric sulfate to afford (+) 3S4R-N-methyl-N-benzoylmethyl-2,3 epoxy cinnamide(4*)

v) treating the above compound 4 with basic catalyst to give the cyclized product (−) clausenamidone(5*), base catalyst may be selected from lithium hydroxide, sodium hydroxide, potassium hydride, lithium diisopropyl amide, butyl lithium, tetraalkyl ammonium hydroxide or trialkyl amine. The solvent in the reaction may be selected from water, menthnol, ethanol, low molecular alkanol, or aqueous alkanol.

vi) reducing compound(5*) with boronhyde class of reducing agent such as lithium boronhydride, sodium boronhydride, lithium tris sec-butyl boron hydride to give (−) 3S, 4R, 5R, 6S levoclausenamide I*.

Note: sign* meaning optically active, R is alkyl.

The Levoclausenamide (prepared by scheme 1) of the present invention may also be prepared by biocatalytic resolution of the starting material racemic methyl 2,3 epoxy cinnamate with hydrolase producing microorganisium to give (+) 2S3R-methyl 2,3 epoxy cinnamate in scheme 2, then repeating the steps iii)–vi) in Scheme 1, thereby obtaining levoclausenamide.

Scheme 2

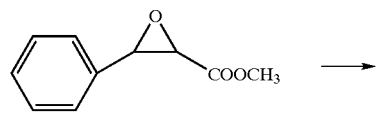

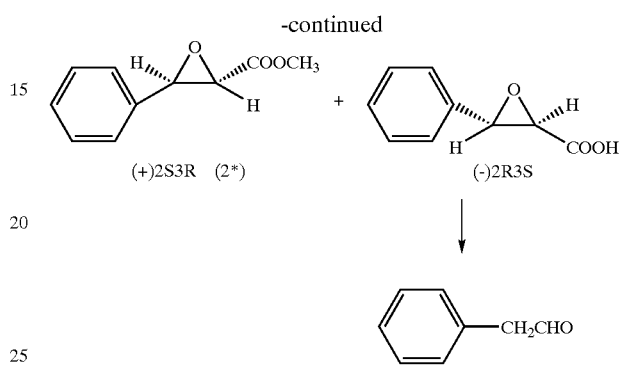

In scheme 2, The hydrolase producing microorganisium used may be selected from such as fungi (e.g. Aspergillus, sp; Mucor sp; Penicillium, sp;Phizopus, sp), bacteria (e.g. Achromobacter, sp; Alcaligenes, sp; Bacillus, sp; Brevibacterium, sp; Corynebac-terium, sp; Erwinia, sp; Pseudomonas, sp), yeast (e.g. Canadida, sp;Pichia, sp), Rhodotorula, sp; Hansenula, sp) or Actomycetals (e.g. Nocardia, sp; Strep-tomyces, sp). The above mentioned microorganisium may be cultured under aerobic condition in medium containing carbon, nitrogen source with appropriate inducer and inorganic salt at room temperature or heating, preferably at 20–40° C., PH5–8,the mycelium produced is collected for stereo-selective hydrolysis of racemic methyl 2,3 epoxy cinnamate as shown in scheme 2.

To the above mentioned culture medium surface active agent such as polyethylene glycol, tween, polyvinyl alcohol, hexadecyl-trimethyl ammonium bromide at concentration of 0.5–5%, preferably 0.5–2% may be added, if necessary.

The stereoselective hydrolysis is proceeded in appropriate organic solvent such as benzene, toluene, xylene, ethylether, ethyl acetate, isopropyl ether, carbon tetrachloride, chloroform preferably toluene, xylene or isopropyl ether, and in such condition that the concentration of substrate as 0.05–10%, preferably 0.5–5%, 10–50° C. of temperature, PH 5–10, preferably 6–9.

Furthermore, the above mentioned enzymatic hydrolysis is carried out in aqueous buffer solution or in both of biphasic aqueous buffer and organic solvent such as toluene, benzene, ether, ethyl acetate, isopropyl ether, toluene, carbon tetrachloride or chloroform, preferable toluene, xylene, or isopyl ether.

The isolation of the optical active methyl 2,3 epoxy cinnamate as product is conducted by the known process in the art, such as, extracting the reaction mixture with organic solvent or separating the organic layer in case of biphasic reaction being applied, washing the organic extract or organic layer with saturated sodium bisulfite solution to remove the phenylacetaldehyde, drying, concentrating to give compound 2, (+) 2S3R, mehyl 2,3 epoxycinnamate.

The levoclausenamide (prepared by scheme 1 or scheme 2) of the present invention may also be prepared by resolution of the intermediate, racemic clausenamidone. The details is shown in scheme 3.

Scheme 3

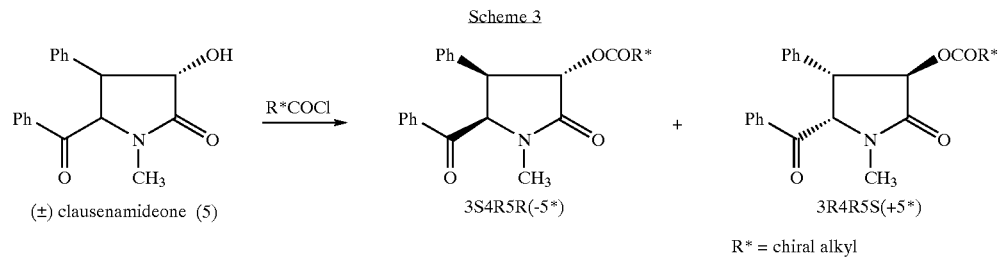

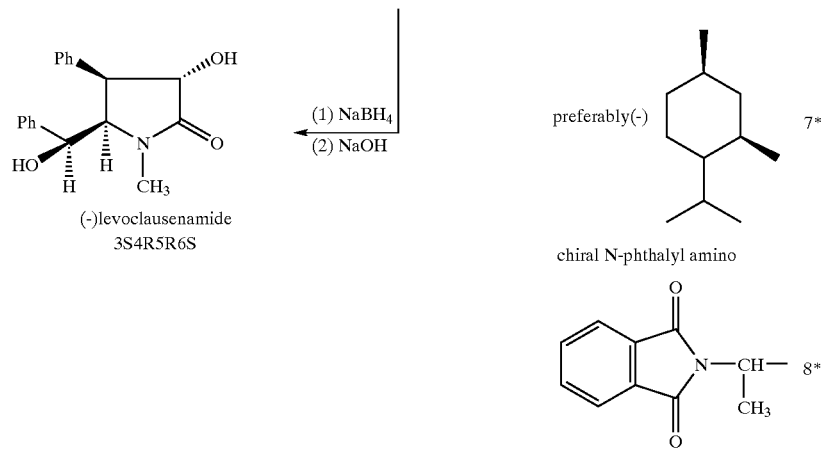

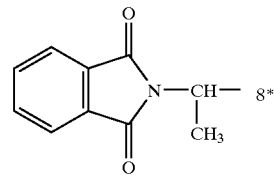

In scheme 3, the resolving agent is selected from chiral acid chloride such as optically active alkyoxy substituted acylhalide, N-phthalyl optical active amino acid halide, or optical active sulfonyl halide, preferably menthoxy active chloride, N-phthalyl (−) alanyl chloride. said resolution comprising following steps:

i') easterifying racemic clausenamidone with optical active acyl chloride in the presence of pyridine,
ii') separating the distereomers (−5*)(+5*) by recrystallization or column chromatography.
iii') reducing (−5*) by sodium borohydride followed by hydrolysis in the presence of NaOH, giving levoclausenamide (−I*)

The present invention is further directed to the method of preparation of optically active clausenamide derivatives of the general formula II selected from one of the following compounds.

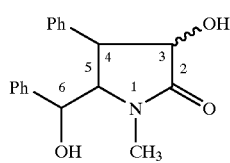

II

3S4R5S6R (−)neoclausenamide,
3R4S5R6S (+)neoclausenamide
3S4R5S6S(−)epineoclausenamide,
3R4S5R6R(+)epineoclausen amide
3S4S5S6R (+)cisclausenamide,
3R4R5R6S (−)cisclausenamide
3S4S5S6S (+)cisepiclausenamide,
3R4R5R6R (−)cisepiclausenamide
3S4S5R6S (−)cisneoclausenamide,
3R4R5S6R (+)cisneoclausenamide
3S4S5R6R(−)cisepineoclausenamide, and
3R4R5S6S(+)cisepineoclausen-amide.

wherein the process may be summarized in following Scheme 4

Scheme 4

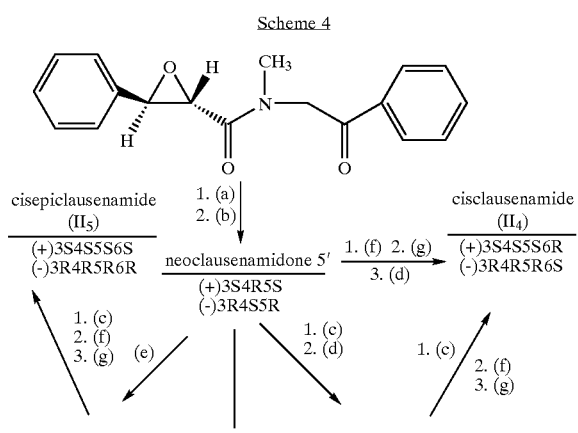

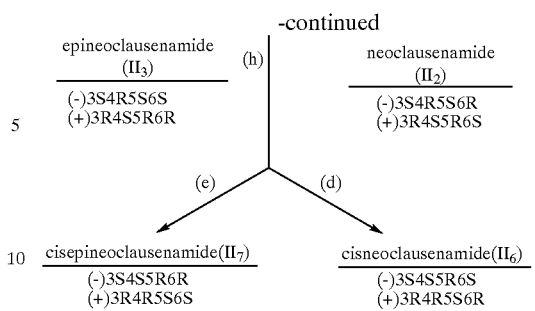

Note:
(a) base catalyzed cyclization, NaOCH₃ or (CH₃)₄NOH
(b) resolution, resolving agent (-)menthyoxyl acetyl chloride
(c) derivation of $C_3$—OH by dihydropyan or acetylchloride/pyridine
(d) reduction of $C_6$=O by reducing agent NaBH₄ or L-selectride
(e) reduction of $C_6$=O by reducing agent Al(i-C₃H₇O)₃
(f) oxidation of $C_3$—OH by oxidizing agent, K₂Cr₂O₇/H⁺, or KmnO₄ + CuSO₄, MnO₂ or DMSO/(COCl)₂
(g) reduction of [2,3] by NaBH₄/H⁺, or NaBH₄/AlCl₃, or catalytic hydrogenation
(h) invertion of $C_3$—OH by DIAD or DEAD/TPP, H⁺ (Mitsunobu method) or by CsOAc/18-crown-8 or the process for preparation of epiclausenamide is showed in scheme 5:

Scheme 5

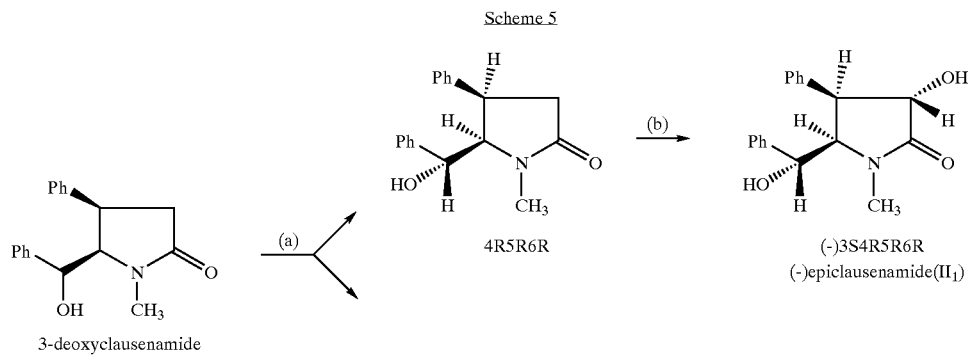

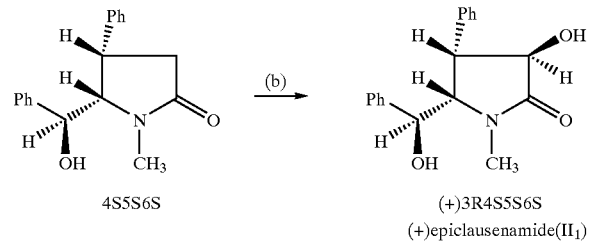

Note:
(a) resolution of racemic 3-dioxyepiclausenamide by chiral optical active acid such as (-) menthyloxy acetic acid, N-phthalyl s-alamine, O-acetyl-mandelic acid
(b) hydroxylation of $C_3$ by LDA/P(OEt)₃/O₂
(c) starting material racemic 3-deoxyepiclausenamide is known and obtained by the known method in the art.

According to the present invention, the following optically active clausenamide derivatives having following physico-chemical features have been obtained.

| Compound | Absolute configuration | mp ° C. | $(\alpha)^L_D$ (c, solvent) |
|---|---|---|---|
| (−)clausenamide | 3S, 4R, 5R, 6S | 161–162 | −146 (0.21, MeOH) |
| (+)neoclausenamide | 3R, 4S, 5R, 6S | 186–187 | +89.5 (0.2, MeOH) |
| (−)neoclausenamide | 3S, 4R, 5S, 6R | 186–187 | −88.6 (0.18, MeOH) |
| (+)epiclausenamide | 3R, 4S, 5S, 6S | 108–110 | +201 (0.245, MeOH) |
| (−)epiclausenamide | 3S, 4R, 5R, 6R | 107–109 | −204 (0.445, MeOH) |
| (+)epineoclausenamide | 3R, 4S, 5R, 6R | 220–222 | +36.5 (0.15, MeOH) |
| (−)epincoclausenamide | 3S, 4R, 5S, 6S | 221–222 | −37.7 (0.16, MeOH) |
| (+)cisclausenamide | 3S, 4S, 5S, 6R | 197–199 | +6.30 (0.46, CHCl$_3$) |
| (−)cisclausenamide | 3R, 4R, 5R, 6S | 196–198 | −6.07 (0.675, CHCl$_3$) |
| (+)cisepiclasuenamide | 3S, 4S, 5S, 6S | 198–199 | +39.7 (0.785, CHCl$_3$) |
| (−)ciscpiclausenamide | 3R, 4R, 5R, 6R | 199–202 | −38.37 (0.66, CHCl$_3$) |
| (+)cisneoclausenamide | 3R, 4R, 5S, 6R | 164–166 | +66.7 (0.46, MeOH) |
| (−)cisneocluasenamide | 3S, 4S, 5R, 6S | 168–170 | −65.3 (0.32, MeOH) |
| (+)cisepineoclausenamide | 3R, 4R, 5R, 6S | 275–277 | +31.2 (0.31, DMSO) |
| (−))cisepineoclausenamide | 3S, 4S, 5R, 6R | 271–273 | −33.3 (0.34, DMSO) |

The present invention is further directed to the facilitating learning and memory activity and inducing long-term potentiation of some optically active clausenamide derivatives. Their nootropic action was 5–10 times and 50–100 times more than that of (±)-clausenamide and piracetam respectively. For example, (−)clausenamide could also improve spatial memory impairment induced by β-amyloid (A β 25–35). The nootropic mechanisms may be deduced as follows:

1. (−) clausenamide was a potassium channel blocker which induces an increase of intracellular $Ca^{2+}$ level and then actiate cAMP and PKC to facilitate memory and LTP.
2. (−) clausenamide increased synapses density in weaning mice and mossay fiber sprouting in adult rat hippocampus.
3. (−) clausenamide increased Ach content and ChAT activity in cortex, hippocampus and striatum.
4. (−) clausenamide increased protein biosyntheses of mice brain and promoted zif/268 mRNA and protein expression.

According to the present invention, some new optically active clausenamide derivatives of the invention unexpectedly shows the improvement of hydpoxia, nootropic, neurodegerrerative diseases such as cerebral ischemia, Alzheimer diseases, vascular and antiazonit action of neurocell apoptosis. In particular, for example, (−) clausenamide at concentration of $10^{-7}$–$10^{-5}$ mol/l inhibited apoptosis significantly In three apoptotic models,. Further studies indicates that the inhibitory of (−) clausenamide on apoptosis may be relevant with its activity in respect of promoting Bcl-2 expression, raising the mitochondrial complex I and complex IV activity and inhibitory release of cytochrome C.

Figure 1:
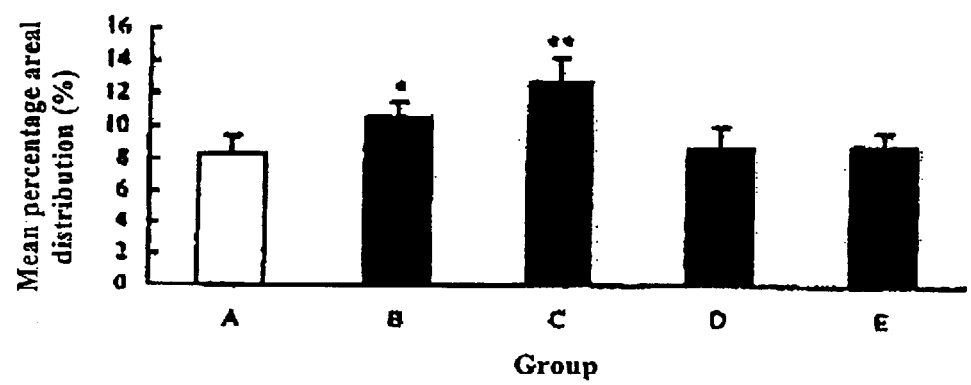
FIG. 1 represents that areal distribution of mossy fiber sprouting in the fascia dentata of rats from control group (A), (−)-Clausenamide (8 mg/kg) group (B), (−)-Clausenamide (40 mg/kg) group (C), (+)-Clausenamide (8 mg/kg) group (D), (+)-Clausenamide (40 mg/kg) group (E). *P<0.05, **P<0.01 vs control group.

The examples which follow are intended to illustrate certain preferred embodiment of the invention, and no limitation of the invention is implied.

EXAMPLE 1

Determination of the Absolute Configuration of Levoclausenamide (−)Clausenamidonyl (−)menthy oxyacctate (−7*) m.p.177–178° C., [α] $^1D^8$=−249(c 0.21,CHCl$_3$) was prepared and its single crystal was analyzed by x-ray diffraction. From the x-ray diffraction pattern of the ester(−7*) the configuration of (−) clausenamidone was identified as 3S, 4R, 5R based on the known configuration of the (−) menthyl in the molecular. After hydrolysis of the ester with acid catalyst, gave the (−) clausenamidone,m.p. 191.5–193.5° C., [α] $^1D^8$=−140.9°(c=0.3,CH$_3$OH)

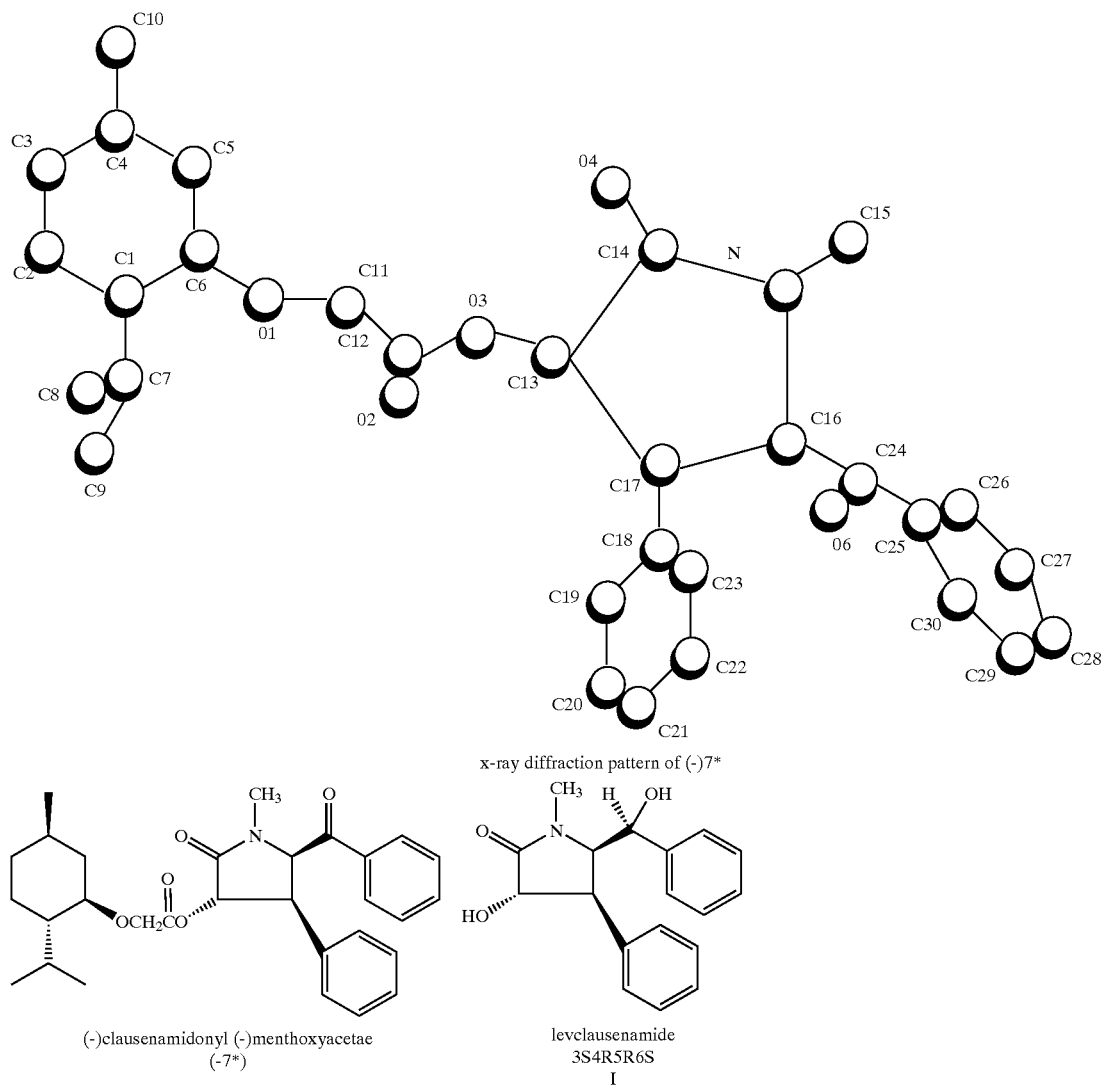

x-ray diffraction pattern of (-)7*

(-)clausenamidonyl (-)menthoxyacetae
(-7*)

levclausenamide
3S4R5R6S
I

Examples 2–8 illustrate synthesis of levoclausenamide as described in scheme 1.

EXAMPLE 2

Preparation of (+)8-β-naphthyl menthyl (+) 2S3R,2,3 epoxy cinnamate (2a*)

Sodium hydride (80%) 430 mg was added to 20 ml dry THF. The solution was gradually dropped to a solution of 1 g benzaldehyde and 2.3 g of (+) 8-β-naphthyl chloroacctate in 10 ml of THF. After the reaction mixture being stirred about 40 min at room temperature, it was poured into 30 ml ice water containing 1 ml of acetic acid and then extracted with ether. The ether extract was washed with saturated $NaHSO_3$ solution followed by saturated $NaHCO_3$ and NaCl solution. It was dried and concentrated to give 2.9 g oily residue. White solid of 1.16 g as title compound was obtained after chromatograph on silica gel column eluted with petroleum ether/ethyl acetate (10:1), yield 79.0%, m.p.38–40° C.,$[\alpha]^1D^5=+35.8°$(c 1.31, $CHCl_3$).

Note: $NaOCH_3$ also can be used.

EXAMPLE 3

Preparation of (+) 2S3R menthyl 2,3 epoxycinnamate(2b*)

A solution of 3.27 g of NaH (80%) in 100 ml anhydrous THF was added dropwise to 11.6 g benzaldehyde and 11.85 g of (+) menthyl chloroacetate in 100 ml dry THF. Afterward it was stirred at room temperature for 10 hrs. Then it was filtered and filtrate was evaporated. To the residue ether was added. The ether solution was washed successively with saturated $NaHSO_3$ aqueous solution, $NaHCO_3$ solution and NaCl saturated solution until neutral. Drying with $Na_2SO_4$, filtered and evaporated to give oily residue which solidified on standing. After recrystallized three times from ethanol yielded 7.62 g (35% yield) of white crystalline solid as title compound, m.p. 62–63° C., $[\alpha]^1D^5=+167°$(c 1.0,$CHCl_3$).

EXAMPLE 4

Preparation of (+) 2S3R N-methyl 2,3 epoxy cinnamate (2*)

To a solution of 4.3 g compound 2*a or 2*b of example 2 and 3 in 80 ml methanol 200 mg of $NaOCH_3$ was added with stirring. After 6 hrs, 0.2 ml HOAc was added, the reaction mixture was concentrated under reduced pressure. The residue was stirred with 100 ml ether for 30 min. Filtring and ether was removed by evaporation. The 4.3 g residue was chromatographed on silica gel eluted with petroleum ether/ethyl acetate (20:1) to give 1.33 g oily product(2*) as title compound, 75% yield, $[\alpha]^1D^5=+170.9°$(c 1.33,CHCl$_3$).

EXAMPLE 5
Preparation of (+)2S3R N-methyl, N-(β-benzylethyl)-2,3 epoxycinnamate(3*)

A solution of 1.78 g compound (2*) of example 4 in 5 ml of methanol and a solution of 1.51 g N-methyl-N-(β-benzyl) ethanol amine in 5 ml methanol was cooled separately to −20° C. and then mixed. To the mixture 100 mg NaOCH$_3$ was added. The reaction mixture was kept in the refrigerator for two days. 0.2 ml of 2N HCl was then added. After removal of the solvent by evaporation 2.3 g of compound (3*) was obtained, yield 77.3%, m.p. 93—93° C., $[\alpha]^1D^5=+70.2°$(c 0.68,CH$_3$OH).

EXAMPLE 6
Preparation of (+) 2S3R N-methyl-N-(benzoyl methyl) 2,3 epoxy cinnamate (4*)

To a solution of 2.97 g compound (3*) in 100 ml of CH$_2$Cl$_2$, was added 2.2 g of CuSO$_4$ and 6.32 g of KMnO$_4$. The suspension was stirred at room temperature for 3 hrs. The reaction mixture was filtered and the filter cake was washed thoroughly with CH$_2$Cl$_2$. The combined filtrate and washing solution was concentrated to yield 2.9 g of oily residue. After crystallization from ethyl acetate/petroleum ether (1:1), 2.3 g(78% yield) of compound (4*) was obtained, m.p. 87° C., $[\alpha]^1D^5=+140.2°$(c 0.5,CH$_3$OH).

EXAMPLE 7
Preparation (−) 3S4R5R clausenamidone (5*)

A solution of 6.6 mg LiOH H2O in 30 ml aqueous methanol was stirred with 2.95 g of compound (4*) at 35° C. for 8 hrs. It was cooled and filtered to give compound (5*) which after recrystallization from methanol ethyl acetate yielded 1.5 g (5*)(51% yield) (−) clausenamidone m.p. 196–198° C., $[\alpha]^1D^5=-338°$(c 0.6,CH$_3$OH)

EXAMPLE 8
Preparation of levoclausenamide(I*)

To a solution of 2.95 g of compound (5*), (−) clausenamidone, 1.52 g of NaBH$_4$ was added while stirring. Afterwards stirring was continued for 3 hrs. Thereafter 1 ml of 2NHCl was added. Then the solvent is removed by evaporation and the residue left behind was dissolved in CH$_2$Cl$_2$. Filtered and concentrated to afford 2.4 g of compound (I*) levoclausenamide yield 81%,m.p. 160–161° C., $[\alpha]^1D^5=-144°$(c=0.2,CH$_3$OH).

Example 9–13 illustrate the biocatalytic resolution of the starting material racemic methyl 2,3 epoxycinnamate to (+) 2S3R methyl 2,3 epoxy cinnamate.

EXAMPLE 9
Resolution of Racemic methyl 2,3 epoxycinnamate by Fungi (asperzillus sp) Enzyme Thirty ml of culture medium of 3% suger, 1% peptone, 0.5% potassium dihydrogen phosphate, 0.5% polyethylene glycol, 1% olive oil in 250 ml flask was sterilized at 120° C. under 1 atm. After cooling it was inoculated with Aspergillus, sp and cultured for 40 hrs at about temperature 30° C. and with 220 rpm. The mycelilium was collected by centrifegalization and was added to 10 ml phosphate buffer solution (pH7) containing 150 mg of (±) methyl 2,3 epoxy cinnamate and the obtained reaction mixture was kept at about 30° C. for 72 hrs. At the end of reaction, the reaction mixture was extracted twice with ethyl acetate (20 ml). The extract was washed with saturated solution of NaHCO$_3$ followed by saturated solution of NaCl, dried with MgSO$_4$ and filtered. The solvent was removed by evaporation. An oily residue 6.6 mg was obtained. It was analyzed by chiral gas chromatograph, which shows ee% 98, $[\alpha]^2D^0=+180°$ (c=1,CHCl$_3$) for (+) 2S3R methyl 2,3 epoxycinnamate.

EXAMPLE 10
Resolution of Racemic methyl 2,3 epoxycinnamate by Yeast Canadida sp Enzyme Thirty milliliters culture medium of 4% surger, 2% peptone, 1% potassium dihydrogen phosphate, 2% polyethylene glycol, 1% olive oil in 250 ml flask was sterilized at 120° C. and under 1 atm for thirty min. It was inoculated with cyclic yeast Candida sp and kept at 30° C., with 200 rpm for 40 hrs. The mycilium was separated and added to 300 mg of racemic methyl 2,3 epoxycinnamate in 30 ml of phosphate buffer solution (pH8). After 72 hrs at 30° C., the reaction mixture was treated as described in example 9 to give 120 mg of (+) 2S3R methyl 2,3 epoxycinnamate with ee%98, $[\alpha]^2D^0=+180°$(c=1,CHCl$_3$).

EXAMPLE 11
Resolution of Racemic methyl 2,3 epoxycinnamate by Bateria Achromobacter sp Enzyme Thirty millilitres culture medium containing 2.5% sodium citrate,1% soybean peptone,0.5% potassium dihydrogen phosphate,2.5% polyethylene glycol,1% olive oil was sterilized at 120° C. and under 1 atm for 30 min. The culture medium was inoculated with cyclic Achromobacter sp. and incubated at 40° C. with 299 rpm for 40 hrs. The mycilium was separated and added to 19 ml phosphate buffer solution (pH7) containing 150 mg of racemic methyl 2,3 epoxycinnamate. After 72 hrs at 30° C. the reaction mixture was treated and analyzed as described in example 9 to yield 66 mg of oily substance, (+)2S3R methyl 2,3 epoxycinnamate with ee%99, $[\alpha]^2D^0=+181°$(c=1,CHCl$_3$).

EXAMPLE 12
Resolution of Racemic methyl 2,3 epoxycinnamate by Bacteria, Bucillus sp Enzyme Thirty millilitres of culture medium containing 20% of lactic acid, 1.5% ammonium sulfate,0.5% potassium dihydrogen phosphate,0.5% polyethylene glycol,0.1% olive oil were sterilized at 120° C. and under 1 atm for 30 min. The culture medium was inoculated with Bucillus sp and incubated at 50° C. with 220 rpm for 40 hrs. The mycilium was collected and added to 150 mg of racemic methyl 2,3 epoxycinnamate in 10 ml phosphate buffer solution (pH=10). The reaction was carried out at 50° C. for 72 hrs. And then treated and analyzed as described in example 9.66 mg of oily product (+) 2S3R methyl 2,3 epoxycinnamate was obtained as ee%99, $[\alpha]^2D^0=+181°$(c=1,CHCl$_3$).

EXAMPLE 13
Resolution of Racemia methyl 2,3 epoxycinnamate by Actomycetales Nocardia sp. Enzyme The 30 ml of culture medium containing 1% of surgar, 20% peptone, 0.3% potassium dihydrogen phosphate,1% polyethylene glycol,2% olive oil in 250 ml flask was sterilized at 120° C. and under 1 atm for 30 min. After cooling, it was inoculated with cyclic Nocardia sp. and incubated at 30° C. with 250 rpm for 36 hrs. The mycilium was collected and added to 220 mg of racemic methyl 2,3 epoxycinnamate in 10 ml buffer solution (pH7.5). The reaction was carried out at 30° C. for 72 hrs. At the end of reaction, the reaction mixture was treated and analyzed as described in Example 9.80 mg of oily (−) 2S3R methyl 2,3 epoxycinnamate was obtained,ee%98, $[\alpha]^2D^0=+180°$(c=1,CHCl$_3$).

Examples 14 and 15 illustrate the preparation of levoclausenamide by resolution of intermediate racemic intermediate clausenamide (Scheme 3)

EXAMPLE 14
Preparation of levoclausenamidone through Resolution of Racemic clausenamidone(Scheme 4)

The mixture of 3 g menthyoxylacetic acid in 10 g $SOCl_2$ was refluxed for 5 hrs and then $SOCl_2$ was removed. Five milliliters of toluene was added and evaporated at reduced pressure to drive the residual $SOCl_2$. 3.5 g brownish residue was dissolved in 50 ml $CH_2Cl_2$ and to which 2 g racemic clausenamidone(±5) was added. Pyridine 1 ml was added while cooling, and stirred 4 hrs at room temperature. Two spots were showed by TLC. The reaction mixture was washed successively with 2N HCl, saturated $NaHCO_3$ aqueous solution, saturated NaCl aqueous solution and dried over $Na_2SO_4$. After removing the solvent 5.4 g of bromnish solid was obtained. After first recrystallization from methanol to give −7*, the mother liquid was chromatographed on silica gel column eluted with ethyl ether/hexane (2:1) to give +7* and more −7*.

(−7*): 1.06 g, yield 30.9%(theoretical yield 50%), m.p.:177–178° C., $[\alpha]^1D^8=-249°$(c 0.21,$CHCl_3$).

(+7*): 0.86 g, yield 24.8%(theoretical yield 56%), m.p.:1.52–153° C., $[\alpha]^2D^0=+156°$(c 11,$CHCl_3$).

(−7*) and (+7*) were hydrolyzed separately in 30 ml methanol catalyzed by PTS. After refluxing for 2 hrs. Methanol was taken off by evaporation and the residue was dissolved in $CH_2Cl_2$. The $CH_2Cl_2$ solution was first washed with acid and followed by base and water.(−) clausenamidone(−5*) and (+) clausenamidone(+5*) was obtained respectively from (−7*) and (+7*) after removal of solvent.

(−)clausenamidone(+5) yield 88%, m.p.:193–194° C., $[\alpha]^1D^8=-340°$(c=0.22,$CH_3OH$).

(+)clausenamidone(−5) yield 82%, m.p.:193–194° C., $[\alpha]^1D^8=+339°$(c=0.21,$CH_3OH$).

(−)clausenamidone(−5*) 0.59 g was reduced as described in Example 8 with 0.11 g $NaBH_4$. Recrystallization from methanol of the product gave 0.5 g of levoclausenamide, yield 83%, m.p.:162–163° C., $[\alpha]^1D^8=-145°$(c=0.24, $CH_3OH$).

EXAMPLE 15
Resolution of Racemic clausenamidone (Scheme 5)

A solution of 3.56 g N-phthayl (−) L-alanine and 5 g of $SOCl_2$ in 50 ml toluene was refluxed for 6 hrs. Toluene and $CH_2Cl_2$ were removed under reduced pressure. To the renction mixture 20 ml toluene was added again and evaporated to drive the residual $SOCl_2$. Then 100 ml of $SOCl_2$ was added and cooled to <0° C.

To above solution racemic clausenamidone 5 g was added under cooling and stirring and followed by adding 1.6 g pyridine dropwise. The reaction mixture was stirred for 10 hrs at room temperature. After 30 ml water was added and the organic layer was separated. The aqueous layer was extracted with 30 ml $CH_2Cl_2$.The extract and organic layer was combined and washed with 30 ml of 2N HCl,saturated $NaHCO_3$ aqueous solution and NaCl aqueous solution. Dried over $Na_2SO_4$ and filtered. The solvent was removed. The residue was recrystallized with ethyl acetate to give cubic crystalline product 1.42 g .yield 21%(theoretical yield 56%),m.p.:189–190° C., $[\alpha]^1D^5=-241°$(c 0.5,$CHCl_3$)(−7).

The crystal was dissolved in 200 ml methanol, then reduced with 1.52 g $NaBH_4$ under stirring for 5 hrs at room temperature. After 1 ml 2NHCl was added and concentrated under reduced pressure. The residue was recrystallized to give 2.38 g of levoclausenamide, yield 81%,m.p.:161–163° C., $[\alpha]^2D^0=-144.4°$(c=0.46,$CH_3OH$).

Examples 16–19 illustrated the method concerning the preparation of some new optically active clausenamide derivative (Scheme 4 and 5) but not limited

EXAMPLE 16

Resolution of Racemic neoclausenamidone 5'

(±)Neoclausenamidone 2.66 g was added to 30 ml $CH_2Cl_2$ solution of menthyoxy acetyl chloride prepared from 2.71 g of the acid. The solution was cooled by ice-water and 1.5 ml of pyridine was added. Stirred at room temperature for 5 hrs. Then the reaction mixture was dilute with 50 ml $CH_2Cl_2$ and was washed with 2N HCl,saturated $NaHCO_3$ solution, 50 ml NaCl solution successively. Dried with $Na_2SO_4$ and concentrated to give 6 g of oily product which is solidified by adding 250 ml of hexane. The solid was filtered and recrystallized with methanol to give 1.49 g of $C_3$-ester(a), m.p.:170–172° C., $[\alpha]^1D^5=-50.9°$(c 1.25, $CHCl_3$), yield 34%(theoretical yield 50%). The hexane and methanol filtrate was chromatographed on silica gel column to give $C_3$-ester (b), m.p.:104–105° C., $[\alpha]^1D^5=-31.2$(c 1.4,$CHCl_3$), yield 40%. The above ester (a) and ester(b) were hydrolyzed as described in example 14 From 6 g of ester (a) gave 3.25 g, 86% yield of (−) neoclausenamidone (−5'*)(3R4S5R). m.p.:164–167° C., $[\alpha]^1D^5=14.9°$(c 0.6, $CHCl_3$) From 5.5 g of ester (b) gave 3.0 g, 89% yield of (+) neoclausenamidone(+5'*)(3S4R5S). m.p.:167–169° C., $[\alpha]^1D^5=+14.1°$(c 0.56,$CHCl_3$)

EXAMPLE 17

Preparation of Optical Active cisclausenamide from Optical Active neoclausenamidone(5'*)

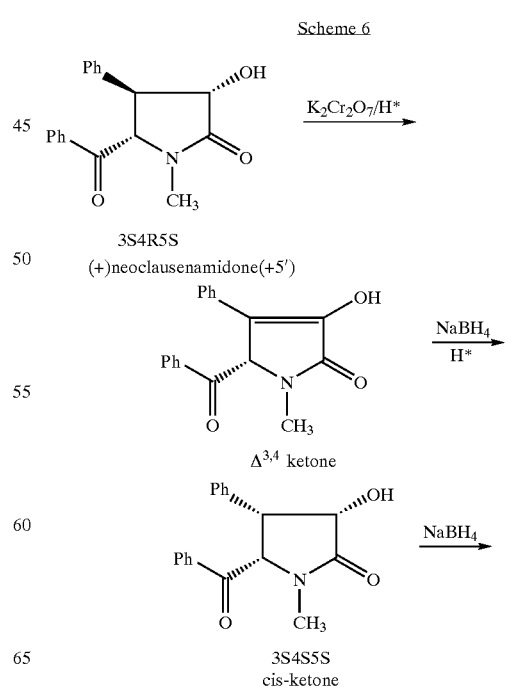

Scheme 6

3S4R5S
(+)neoclausenamidone(+5')

$\Delta^{3,4}$ ketone

3S4S5S
cis-ketone

-continued

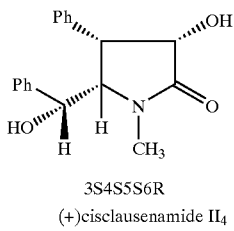

3S4S5S6R
(+)cisclausenamide II₄

An acidic $K_2Cr_2O_7$ solution made from 0.66 g $K_2Cr_2O_7$ and 0.66 g concentrate $H_2SO_4$ and 5 ml of water was added to a solution 0.25 g of (+) neoclausenamidone in 10 ml $CH_2Cl_2$ with stirring at 25–30° C. After stirring for about 5 hrs. 20 ml of $CH_2Cl_2$ was added. The organic layer was separated and washed with a saturated $NaHCO_3$ solution followed by water. The solvent was taken off, the obtained solid was recrystallized with methanol to give 0.19 g(yield 78%) of $\Delta^{3,4}$ neoclausenamidone,m.p. 157–159° C., $[\alpha]^1D^5=-199.6°(c\ 0.75,CHCl_3)$.

The above product 0.10 g was dissolved in 10 ml $CH_2Cl_2$ containing 1 ml acetic acid, 0.01 g of $NaBH_4$ was added by fraction with stirring. The reaction was monitored by TLC. At the end of reaction, acetic acid dropwise to react with excess $NaBH_4$ left. Then 20 ml $CH_2Cl_2$ was added and the reaction mixture was poured in to 50 ml of ice water. The organic layer was separated and washed with a saturated $NaHCO_3$ solution and water. The solution was evaporated and the residue was chromatographed on silica gel to give 0.074 g, yield 73% of cis-ketone, m.p. 145–147° C., $[\alpha]^2D^0=+111.0°(c\ 0.48,\ CHCl_3)$.

The cis-ketone 0.08 g was dissolved in 10 ml $CH_2Cl_2$ and reduced with 0.01 g of $NaBH_4/CH_3OH$. At the end of reaction 30 ml of $CH_2Cl_2$ was added followed by acetic acid to react with excess $NaBH_4$. The organic layer was washed with a saturated solution of $NaHCO_3$ and then water. The solvent was evaporated to leave an oily residue. It was crystallized with acetone and petroleum ether, and the crystalline of solid (+) 3S4S5S6R cisclausenamide 0.59 g (77%) with m.p. 197–199.5° C.,$[\alpha]^2D^2=+6.30°(c\ 0.46, CHCl_3)$ was obtained.

The above procedure was applied to the preparation of (−) 3R4R5S6R cisclausenamide from (−) neoclausenamidone(−5'). The corresponding $\Delta^{3,4}$ clausenamidone obtained yield 75%,m.p. 154–156° C., $[\alpha]^1D^5=+206.8°(c\ 0.90,CHCl_3)$, cis ketone 3R4R5R yield 76%, m.p. 130–132° C., $[\alpha]^2D^0=+116.5°(c\ 0.40,CHCl_3)$, (−)cisclausenamide 3R4R5R6S yield 69%, m.p. 196–198° C., $[\alpha]^2D^2=-6.07°(c\ 0.67,CHCl_3)$ EXAMPLE 18
Preparation of Optical Active epiclausenamide II₁(See Scheme 5)

To a solution of 60 mg 3-deoxyepiclausenamide in 30 ml $CH_2Cl_2$ was added 621 mg of O-acctylmandelic acid, 26 mg of 4-dimethyl-aminopyridine and 880 mg of 1,3 dicyclohexyl carbodimide. The reaction mixture was stirred 1 hr at room temperature. It was filtered and the filler cake was washed successively with 5 ml of 2N HCl,saturated solution of $NaHCO_3$ and NaCl solution. After dried with $Na_2SO_4$,the solvent was taking off by evaporation. The oily residue was chromatographyed on silica gel column eluted with ethyl acetate/petroleum ether (1:2) and recrystallized from ethyl acetate to give two products: A, m.p.:212–215° C., yield 46%.B, m.p.:206–209° C., yield 47%. A and B were hydrolyzed separately in mixtures of $CH_3OH$ and 10 ml $CH_2Cl_2$ in the presence of 141 mg of $K_2CO_3$ at room temperature for 12 hrs. The reaction mixtures were treated as usual. From A(yield 93%) of (+) 3-deoxyepiclausenamide m.p.:239–242° C.,$[\alpha]^3D^0=+137(c\ 0.46,\ CH_3OH)$ and from B(yield 90%) m.p.:237–240° C.,$[\alpha]^3D^0=-136(c\ 0.48, CH_3OH)$ The optical active 3-deoxyepiclausenamide (120 mg) was dissolved in a mixture of 5 ml THF and 1.3 ml HMP. The solution was cooled −70° C.,and stirred for 5 min, and then 1.40 ml $LDA((C_2H_5)_3NLi)$ was added and stirred 1 hr at −60 to −70° C. under nitrogen. The above solution turned red, and 53 $\mu l\ P(OEt)_3$ were added. The reaction was taken place under a stream of dried oxyen at −60 to −70° C. for 2 hrs. At the end of reaction, the reaction mixture were adjusted to pH3–4 with 0.5N HCl in an ice bath. The reaction mixture were extracted with ethyl acetate four times,20 ml each time. The organic layer then washed with saturated NaCl solution and dried with $Na_2SO_4$.The solvent was driven off by evaporation to give an oily residue which was chromatographed on silica gel column eluted with ethyl acetate/petroleum ether (1:3) followed by recrystallization with ethyl acetate. Optical active epiclausenamide was obtained.

From (−) 3-deoxyepiclausenamide: (−) epiclausenamide (−II₁) was obtained in 38% yield,m.p.107–109° C.,$[\alpha]^2D^0=-204(c\ 0.45\ CH_3OH)$ From (+) 3-deoxyepiclausenamide:(+) epiclausenamide(+II₁) was obtained in 28% yield, m.p.108–110° C.,$[\alpha]^2D^0=+201(c\ 0.25\ CH_3OH)$ EXAMPLE 19
Preparation of Optical Active cis neoclausemanide and cisepineoclausenamide II₇ Scheme 4)

(1) DEAD(diethyl azodicarboxylate) 2.10 ml was added slowly to a solution of 1.5 g (−) 3R4S5R neoclausenamidone, 2.6 g of triphenylphospine and 0.99 g of $ClCH_2COOH$ in 50 ml of toluene. The reaction mixture was stirred at room temperature for 12 hrs. And then treated with a mixture solvent of ethyl acetate and petroleum ether, and filtered. The filter cake was washed thoroughly with ethyl acetate. The combined filtrate and washing was evaporated. The residue with ethyl acetate/petroleum ether was collected and the solvent was taken off by evaporation. The solid left behind without further purification was stirred with 750 mg p-toluene sulfonic acid in 3 ml of methanol at room temperature for 18 hrs. The methanol was evaporated and the residue was dissolved in $CH_2Cl_2$. The organic layer was washed first with $NaHCO_3$ until the washing being slightly basic and then followed by saturated solution of NaCl. After taking off the solvent by evaporation, the residue was chromatographed on silica gel luted with ethyl acetate/petroleum ether (1:1) to give 1.05 g (70%yield). After recrystallization from petroleum ether/ethyl acetate gave 0.7 g of product (−)3S4S5R cisneoclausenamidone. m.p. 145.8–146.9° C.,$[\alpha]^2D^5=-138.6(c\ 0.812,\ CHCl_3)$.

By the same procedure described above (+) 3S4R5S cisneoclausenamidone yielded (=) 3R4R5S cisneoclausenamidone, m.p. 143.8–145.7° C., $[\alpha]^2D^5=+139.8(c\ 1.74,CHCl_3)$.

(2). Reduction of $C_6$ ketone Obtained from(1)

To a solution of 0.15 g (−) cisneoclusenamidone 3S4S5R in 20 ml Of methanol, o.o41 g of NaBH4 was added gradually, with stirring after the reaction mixture was stirred at room temperature for three hours, the reaction mixture was neutralized with acetic acid. Then it was pound to a mixture of 50 ml CH2Cl2 and 20 ml ice water. The organic layer was washed with saturated NaHCO3 aqueous solution and dried over Mg2SO4, After evaporating off the solvent. The white solid residue was chromatographed on silica geil to give 0.04 g A after recrystallization from ether to give (−) cisneoclusenamide 3S4S5R6S mp. 168–17020 C.,$[\alpha]^3D^0=-$ 65.3 (C,0.32,MeoH) and from B, 0.075 g of (−)cisepineoclusenamid 3S4S5R6R after recrystallization from methanol, with m.p. 271–273° C., $[\alpha]^3D^0=-33.3$ (C,0.34, DMSO).

With the same procedure using (+) neoclusenamide give (+)cisneoclusenamide m.p. 164–166° C., $[\alpha]^3D^0=+66.7$(C, 0.32, MeoH, and (+) cisepineoclusenamide mp. 275–277° C., $[\alpha]^3D^0=+31.2$ (C,0.34, DMSO)

EXAMPLE 20

The Mechanism of levoclausenamide in Enhancing Synaptic Transmission in dentate gyrus of Rats The rats were anaesthetized with urethane carbonate. The recording and stimulating electrodes were made from Teflon coated stainless steel wires. The bipolar stimulating electrode was sterotaxically placed in the entorhinal cortex to stimulate the perforant path, and the evoked potential was extracellular recorded from the dentate gyrus granule cell layer of ipsilateral. The population spike (PS) is served as an indication of granule cell's excitation. Long term potentiation (LTP) was induced by a 200 $H_z$ high frequency stimulation 5×single square wave pulses of 0.2 ms duration. The drug or vehicle (DMSO) were injected into lateral cerebral ventricle in a 5 µl volume over a 5 min period via a Hamilton syringe.

1. It was demonstrated in our study that both NMDA receptor and VDCC(Voltage-dependent calcium channel) involved in the LTP induced by high (200 $H_z$) frequency stimulation in the dentate gyrus of anesthetized rats, and the levoclausenamide-induced potentiation of synaptic transmission completely depended on VDCC. Accompanying these two kinds of potentiation of synaptic transmission, the activity of calcineurin and capain in the hippocampal and cortical tissues increased. These results (as shown in Tables 1 and 2) suggest that levoclausenamide potentiate the synaptic transmission in anesthetized rat through a mechanism different from that involved in HFS-induced LTP, but the phosphorylation and dephosphorylation of protein may be a common process involved in these two mechanisms.

Figure 2:
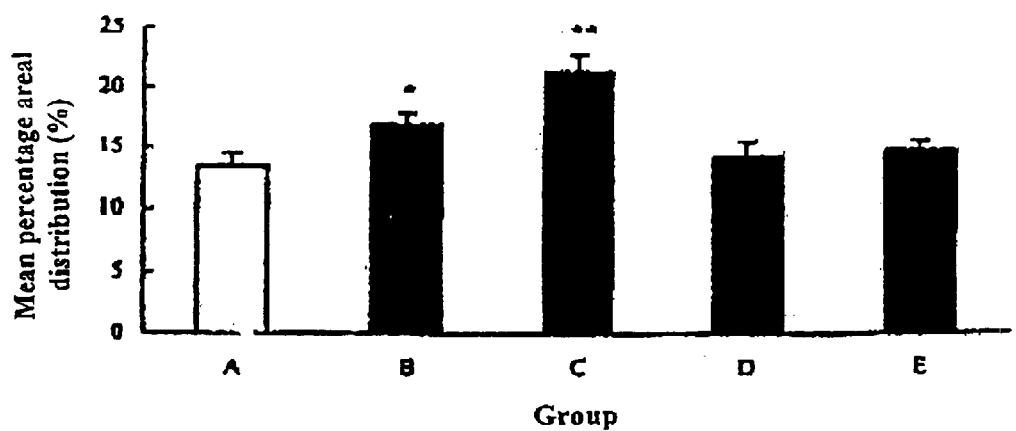
FIG. 2 represents that areal distribution of mossy fiber sprouting in the hippocampal CA3 region of rats from control group (A), (−)-Clausenamide (8 mg/kg) group (B), (−)-Clausenamide (40 mg/kg) group (C), (+)-Clausenamide (8 mg/kg) group (D), (+)-Clausenamide (40 mg/kg) group (E). *P<0.05, **P<0.01 vs control group.

2. It was demonstrated that few mossy fiber sprouting of CA3 and dentate gyrus of hippocampus in adult rat can be seen. However, levoclausenamide at dosage of 8 and 40 mg·kg$^{-1}$, orally-administrated daily for 10 days, dose-dependently increased the mossy fiber sprouting in the fascia dentate and stratum lucidum. But (+) clausenamide showed no significant effect on the mossy fiber sprouting in these two areas. This is morphological basis for levoclausenamide to incnease synaptic transmission (see FIGS. 1 and 2).

Figure 3A:
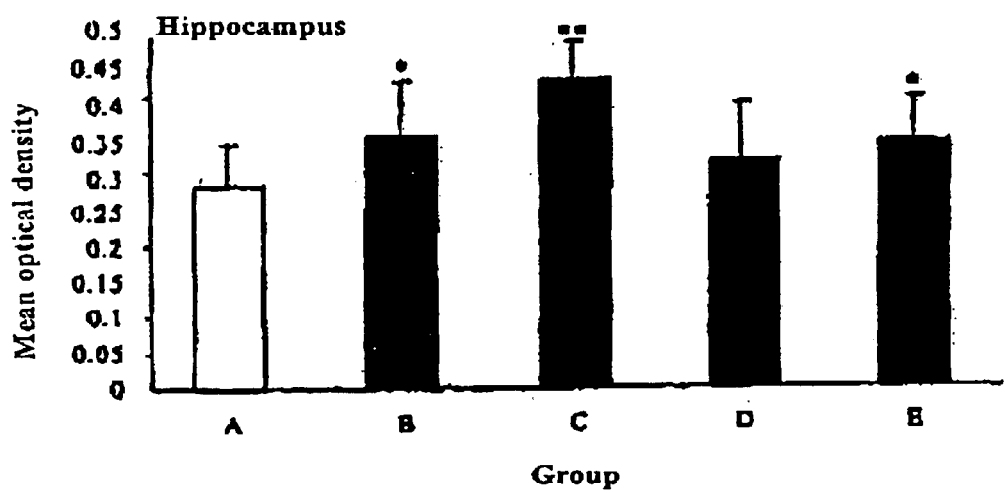
FIG. 3A and FIG. 3B represent that Relative amount of BDNF protein expressed in the hippocampal pyramid cells and parietal cortical neurons of rats from control group (A), (−)-Clausenamide (8 mg/kg) group (B), (−)-Clausenamide (40 mg/kg) group (C), (+)-Clausenamide (8 mg/kg) group (D), (+)-Clausenamide (40 mg/kg) group (E). *P<0.05, **P<0.01 vs control group.
Figure 3B:
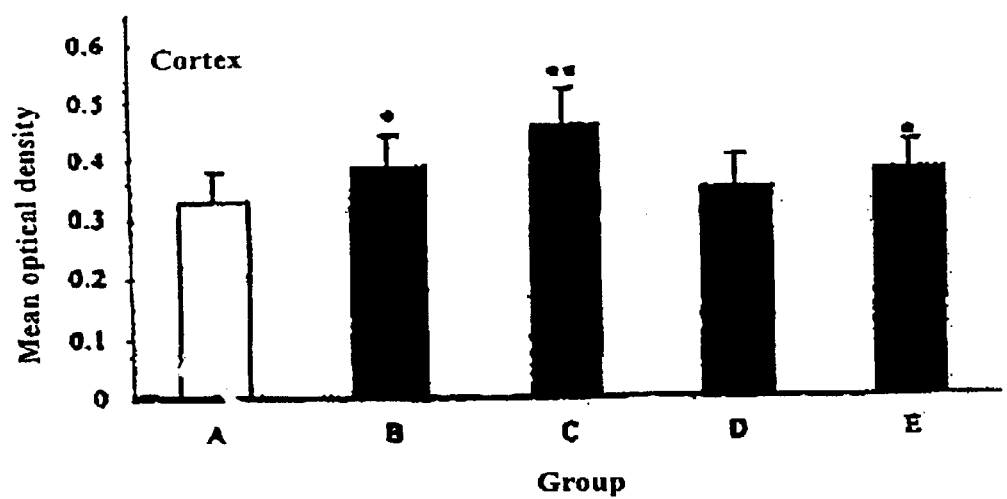
Figure 4:
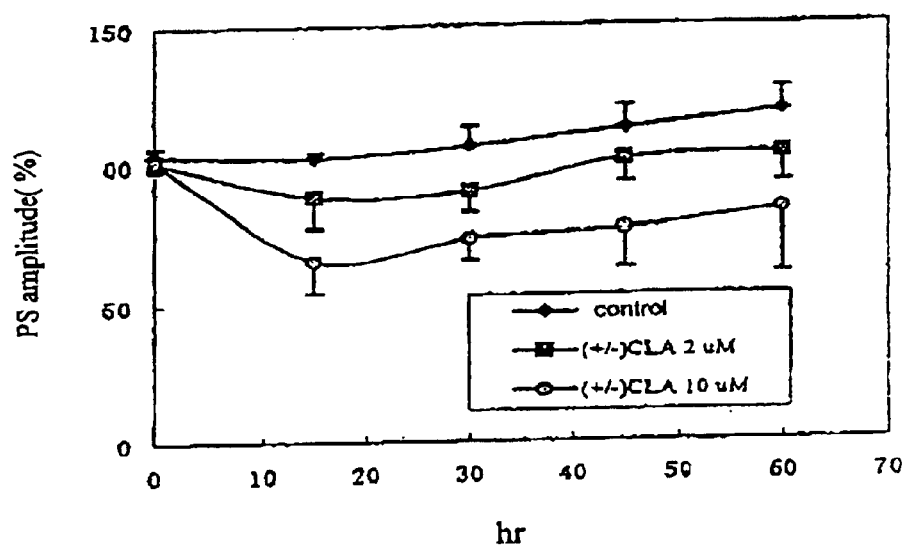
FIG. 4 represent effects of (±) clausenamide at concentration of 2 $\mu$M and 10 $\mu$M on PS amplitude (%)

3. The cortical neurons and granule and pyramide cells in hippocampus of normal rats show a large of BDNF(brain derived neurotrophine factor). levoclausenamide (8, 40 mg·kg$^{-1}$) orally-administrated daily for 10 days, dose-dependently increased the BDNF protein expression in the cortical neurons and pyramide cells in the hippocampus, but (+) clausenamide showed slightly increasing effect only at a dose of 40 mg·kg$^{-1}$, suggesting that the different effects of (−), (+) clausenamide on hippocampal synaptic transmission may be related to their different actions on the BDNF protein expression. The result is shown in FIG. 3.

3. Glutamate, the most abundant excitatory neurotransmitter in the CNS, released from presynaptic site and activated a variety of postsynaptic receptor, and then potentiated synaptic transmission. mGlu R (metabotropic glutamate receptor) indirectly regulates signaling and activats various second messenger cascades. The study on the effect of mGlu antagonist (±) MCPG ((±)-α-methyl-4-carboxyphenylglycine) on the (−) clausenamide-induced LTP in hippocampal DG in vivo showed that (±) MCPG(10 µmol, icv) inhibited the induction of LTP induced by HFS and levoclausenamide, and (±) MCPG 15 min after HFS or levoclausenamide reversed the established LTP. These results syggested that MCPG-sensitive mGlu receptor was necessary for the induction and maintenance of LTP induced by levoclausenamide, and levoclausenamide enhanced synaptic transmission through mGlu receptor.

TABLE 1

The calcineurin activity in the cortical and hippocampal tissue. The activity of calcineurin is expressed as (µmol Pi)/hr/µ g protein. All the values are represented as mean ± S.D. (n = 5), *P < 0.05 vs control group. impairment of memory

| Groups# | Calcineuringical features of Ala | |
| --- | --- | --- |
| | Cortical tissue | Hippocampal tissue |
| Control | 8.3 ± 0.4 | 7.8 ± 0.6 |
| AP5 | 7.9 ± 0.7 | 8.1 ± 0.7 |
| Nimodipine | 8.4 ± 0.5 | 7.7 ± 0.8 |
| HFS | 9.2 ± 1.1 | 8.5 ± 0.7 |
| AP5 + HFS | 8.8 ± 0.7 | 9.6 ± 0.5* |
| Nimodipine + HFS | 7.7 ± 1.4 | 9.8 ± 0.4* |
| AP5 + Nimodipine + HFS | 8.0 ± 0.9 | 7.9 ± 0.7 |
| (−)-Clausenamide | 11.2 ± 0.9* | 10.4 ± 0.5* |
| (−)-Clausenamide + AP5 | 11.6 ± 1.4* | 10.1 ± 0.8* |
| (−)-Clausenamide + Nimodipine | 9.1 ± 1.2 | 8.3 ± 0.6 |

The dose of Nimodipine in related groups is 2 nmol.

TABLE 2

The calpain activity in the cortical and hippocampal tissue. The activity of calpain is expressed as $\Delta A_{595nm}$/hr/mg protein. All the values are represented as mean ± S.D.,(n = 5). *P < 0.05 vs control group, #P < 0.05 vs HFS group.

| Groups# | Calcineurin | |
| --- | --- | --- |
| | Cortical tissue | Hippocampal tissue |
| Control | 1.5 ± 0.2 | 1.7 ± 0.5 |
| AP5 | 1.6 ± 0.4 | 1.6 ± 0.6 |
| Nimodipine | 1.7 ± 0.3 | 1.8 ± 0.5 |
| HFS | 1.8 ± 0.7 | 4.3 ± 0.7** |
| APS + HPS | 1.7 ± 0.4 | 2.9 ± 0.8*# |
| Nimodipine + HFS | 1.8 ± 0.5 | 2.6 ± 0.7*# |
| AP5 + Nimodipine + HFS | 1.7 ± 0.4 | 1.8 ± 0.6 |
| (−)-Clausenamide | 2.6 ± 0.5* | 2.7 ± 0.8* |
| AP5 + (−)-Clausenamide | 2.7 ± 0.6* | 2.6 ± 0.7* |
| Nimodipine +(−)-Clausenamide | 1.6 ± 0.6 | 1.9 ± 0.6 |

The dose of Nimodipine in related groups is 2 nmol.

EXAMPLE 21

Improving Effect of (−) clausenamide on A β Induced Impairment of Memory

Pathological features of Alzheimer's disease (AD) include extensive neuronal loss and the presence of numerous neurofibrillary tangles and senile plaques in the brain. The senile plaques contain amyloid fibrils derived from a 39–43 amino acids peptide referred to as β-amyloid or A β which can produce neurotoxicity. A β 25–35 poccesses the similar neurotoxicity and ability of self-aggregation as A β 1–42. Administrated aggregated A β 25–35 into rat's lateral cerebral ventricle induced memory impairment in Morris water maze.

(−)clausenamide (8,40 mg·kg$^{-1}$), administered daily for 8 days starting from the 8$^{th}$ day after icv injection of 15 nmol aggregated A β 25–35, significantly ameliorated the spatial learning and memory impairment induced by aggregated A β 25–35. The latency for finding the platform beginning from 3$^{th}$ to 5$^{th}$ day in (−)clausenamide 8 mg·kg$^{-1}$ and 40 mg·kg$^{-1}$ groups was shorter than that of A β group. (+) clausenamide in doses of 8 and 40 mg.kg$^{-1}$ and piracetam in dose of 400 mg.kg$^{-1}$ showed no effect. With increasing of training days, the initial heading angle became small. On the 3$^{th}$ day, the initial heading angle of A β group was larger than control. (−) clausenamide at doses of 8 and 40 mg.kg$^{-1}$ significantly reduced the angle. (+) clausenamide at the same doses and piracetam at 400 mg·kg$^{-1}$ showed no improving effects. (see Tab.3)

There are four strategies for finding platform in Morris water maze: random, circle, taxis and line. In the beginning of training the search strategies for finding target is mainly circle and random, with the increasing of training, the percentage of the two strategies declined gradually, Beginning from the 3$^{th}$ day, declining speed in control and (−) clausenamide group was faster than A β,(+) clausenamide and piracetam groups. Meanwhile, the appearance of taxis and line strategies in (−) clausenamide group increased markedly.

TABLE 3a

Effects of (−), (+) Clausenamide on the number of error of β-AP (25–35)-treated rats in one trial passive avoidance.
Value is represented as MEAN ± S.E.M.

| Groups | Number of error | |
|---|---|---|
| | Training | Acquisition |
| Shan-operated + vehicle (n = 8) | 1.6 ± 0.42 | 0.3 ± 0.12 |
| β-AP-treated + vehicle (n = 8) | 2.6 ± 0.71 | 0.9 ± 0.33 |
| β-AP-treated + (−)Clausenamide (8 mg/kg, n = 9) | 3.1 ± 1.22 | 0.7 ± 0.24 |
| β-AP-treated + (−)Clausenamide (40 mg/kg, n = 9) | 4.4 ± 0.87 | 1.1 ± 0.27 |
| β-AP-treated + (+)Clausenamide (8 mg/kg, n = 9) | 3.3 ± 0.42 | 0.8 ± 0.38 |
| β-AP-treated + (+)Clausenamide (40 mg/kg, n = 9) | 3.9 ± 2.3 | 1.1 ± 0.19 |
| β-AP-treated + piracetam (400 mg/kg, n = 8) | 4.1 ± 1.14 | 1.6 ± 0.26 |

A:control; B:A β 25–35, C:A β 25–35+(−)clausenamide at 8 mg/kg; D:A β 25–35+(−)clausenamide at 40 mg/kg; E:A β 25–35+(+) clausenamide at 8 mg/kg; F:A β 25–35+(+) clausenamide at 40 mg/kg; G:A β 25–35+Piracetam at 400 mg/kg

EXAMPLE 22

Inhibitory Effect of (−) clausenamide on Apoptosis in Bax α cDNA High Expressing PC 12 Cell Line 1. The Construction of pcDNA3-bax α Plasmid and its Transfection into the PC12 Cell Line In order to increase the expression level of the transfected gene, we first cut some of the 3' polyA signal sequences from the Bax α cDNA and constructed the intermediate plasmid pBluescript SK-Bax α (pA). Then cut the Bax α cDNA from the intermediate plasmid, religate with the eukaryotic expression plasmid pcDNA3 and obtained the pcDNA3-Bax α recombinant plasmid. The restriction enzyme analysis showed that the Bax α cDNA was inserted in right direction and has the same size. DNA sequences analysis showed that the inserted Bax α has the same nucleotide formation as the original cDNA. The recombinated Bax α has −50 bp of 5' untranslated region(5'-UTR), 576 bp of open reading frame (ORF), and 137 bp of 3' untranslated region (3'-UTR). The 5' methionine translation initiation region has the Kozak consensus sequences. So this plasmid may be used to transform the Bax α gene into the mammalian cells and guarantees highly expression of Bax α by using its strong promoter.

The Lipofectamine transfecting method was used to transfect the pcDNA3-Bax α into the PC12 cell line. G-418 was used to select the resistant cell clones. Western blot analysis and immunohistochemical method showed that the transfected PC-12 cells has a high expression of Bax α protein. This experiment successfully produced the Bax α high expressing PC12 cell line.

2. The Inducement of Bax α High Expressing PC12 Cell Apoptosis and the Effect of (−) Clausenamide Under normal condition, the Bax α high expressing cells had the same natural apoptosis rate with the neo transfected PC12 cells. It indicated that Bax α did not promote cell apoptosis without a death signal. After the 6-OHDA (100 μM) treatment, TUNEL and the flowcytometry method showed that the Bax α high expressing cells had a higher apoptotic rate than those of the vector transfected controls TABLE 3b Effect of A β 25–35 on initial heading angle in Marris water mazw and the action of (−)clausenamide

| Group | Training days | | | | |
|---|---|---|---|---|---|
| | 1 | 2 | 3 | 4 | 5 |
| A | 93.6 ± 34.6 | 76.8 ± 29.8 | 47.3 ± 15.1 | 29.6 ± 10.7 | 15.4 ± 20.4 |
| B | 106.3 ± 29.8 | 98.7 ± 30.4 | 73.6 ± 20.3* | 60.6 ± 23.8* | 46.7 ± 19.4* |
| C | 89.7 ± 29.4 | 72.3 ± 19.8 | 46.5 ± 21.2# | 30.4 ± 14.8# | 17.6 ± 9.5# |
| D | 101.5 ± 24.3 | 83.5 ± 21.8 | 51.2 ± 18.7# | 28.4 ± 13.2# | 20.7 ± 8.7# |
| E | 99.4 ± 31.7 | 93.5 ± 29.6 | 82.1 ± 26.7 | 70.2 ± 21.5 | 59.2 ± 18.3 |
| F | 112.4 ± 32.8 | 102.5 ± 28.7 | 84.2 ± 22.5 | 83.1 ± 26.5 | 65.4 ± 20.8 |
| G | 92.5 ± 28.9 | 87.3 ± 24.2 | 74.6 ± 23.7 | 62.5 ± 19.6 | 44.5 ± 14.3 |

*P < 0.05 vs control;
P < 0.05 vs A β 25–35 group.

(49.96% vs 32.9%), indicating that Bax α plays an important role in inducing apoptosis. (−) Clausenamide $10^{-7}$M, $10^{-6}$M, $10^{-5}$M could significantly lower the apoptotic rate from 49.9% to 36.23%, 28.1% and 9.5% seperately.

3. The Mechanism of Action of (−) Clausenamide in Inhibiting Apoptosis 24 hours after the 6-OHDA treatment, western blot analysis showed that the Bax α high expressing PC12 cells had a lower Bcl-2 level. (−) Clausenamide at to $^{-7}$M, $10^{-6}$M could significantly increase the Bcl-2 expression level. Comparing with the vector transformed control, the mitochondria of the 6-OHDA treated Bax α high expressing cells had a lower level of GSH(9.84±1.20 vs 14.98±1.18 nmol/mg pro) and a higher level of MDA(2.46±0.19, 2.01±0.12 nmol/mg pro). (−) Clausenamide at $10^{-7}$M, $10^{-6}$M, $10^{-5}$M could significantly increase the mitochondrial GSH level (12.29±0.99, 15.10±0.95,17.78±1.04 nmol/mg pro)and lower the mitochondrial MDA level(1.76±0.17,1.54±0.13,1,33±0.11 nmol/mg pro). It means that Bax α expression may promote the production of reactive oxygen species. The antiapoptotic effect of (−) clausenamide may be attributed to its reduction of the mitochondrial MDA level and the increase of mitochondrial GSH level. The increased mitochondrial GSH may be the result of the increased Bcl-2 level. As Bcl-2 itself is not an antioxidant, it may promote the closing of PT pores, and form heterodimers with Bax α and protect the mitochondria from injury and thus reduce the production of reactive oxygen, species. This kind of action is superior to those simple antioxidants.

The Bax α high expressing PC12 cells had a higher mitochondrial membrane potential in comparision with the neo transfected PC12 cells. After the 6-OHDA treatment for 12 hours, the Bax α high expressing PC12 cells showed a significantly low mitochondrial membrane potential (95.08 vs 24.6). (−) Clausenamide at $10^{-7}$M, $10^{-6}$M could increase the collapsed mitochondrial membrane potential significantly to 30.7±3.3 and 56.0±5.0. In comparison with the vector transformed control, the Bax α high expressing PC12 cells showed a significant decrease of the mitochondrial complex I and the complex IV activity (complex I: 1.44±0.16 vs 1.68±0.14 umol/mg pro/min complex IV 0.09±0.019 vs 0.15±0.022 μmol pro/min). (−) Clausenamide at $10^{-7}$M, $10^{-6}$M, $10^{-5}$M could significantly increase the lowered mitochondrial complex I and complex IV activity (complex I:1.57±0.12, 1,98±0.05, 2.16±0.2 umol/mg pro/min; complex IV 0.12±0.015, 0.15±0.02, 0.18±0.01 umol/mg pro/min). Obviously, the increased mitochondrial membrane potential is considered to be one of the antiapoptotic mechanisms of (−) Clausenamide. The increased mitochondrial complex I and complex IV activity may account for the increased mitochondrial membrane potential. The Bax α protein may induce apoptosis by affecting enzyme activities of the mitochondrial electron transfer chain. And the mitochondrial complex I and complex IV could be the targeting points of the Bax α protein.

Studies have shown that the widely existing cytochrome c plays an important role in inducing apoptosis. Cytochrome c is the water soluble cytochrome within the cell and existed at the outside of the mitochondria inner membrane. Cytochrome c could be released into the cytoplasm from the mitochondrial to activate the apoptotic program. This study first purified the His-tagged Bax protein from the bacteria by the Metal Affinity method. When added to the isolated mitochondria, it caused a significant decrease of mitochondrial cytochrome c content (74.43±5.69 ug/mg, pro vs 50.2±3.65 ug/mg pro, p<0.01). (−)Clausenamide at concentrations of $10^{-7}$M, $10^{-6}$M, $10^{-5}$M could significantly decrease the Bax α induced cytochrome c release from mitochondria to 58.73±3.77 μg/mg pro, 61.7±5.3 μg/mg pro and 67.95±7.6 μg/mg pro separately. It means that (−) clausenamide may also act directly on mitochondrial itself to exert its antiapoptotic activity independent Bcl-2. The exact mechanism of action still remains to be determined.

In conclusion: (−) Clausenamide was able to inhibit the apoptosis of the PC12 Bax α cells caused by 6-OHDA. This effect may be related to its action in promoting Bcl-2 expression, raising the mitochondrial complex I and complex IV activity. (−) Clausenamide could also exerts its action on mitochondria itself by inhibiting the Bax α induced release of cytochrome c.

TABLE 4

Effects of (−) clausenamide on memory impairment induced by anisodine in step-down and step-through tests

| Dugs | Doses mg/kg | Error number | | Latencies (sec) | |
| --- | --- | --- | --- | --- | --- |
| | | Step-through | Step-down | Step-through | Step-down |
| 0.9% Nacl | | 12.7 ± 4.6 | 0.9 ± 1.0 | 24.4 ± 59 | 184 ± 105 |
| Piracetam | 500 | 4.1 ± 3.2*** | 0.7 ± 0.5 | 107 ± 110** | 180 ± 110 |
| (−) Clausen-amide | 5 | 5.7 ± 4.7*** | 0.5 ± 0.5 | 47.9 ± 90** | 186 ± 129 |
| | 10 | 6.5 ± 5.0*** | 0.2 ± 0.4** | 59.4 ± 91** | 296 ± 97** |
| | 50 | 7.1 ± 3.6*** | 0.2 ± 0.4** | 17.1 ± 12.4 | 265 ± 91** |

N = 10, $\overline{X}$ ± SD
**P < 0.05
***P < 0.01 vs 0.9% Nacl + anisodine

TAB 5

Effects of piracetam, (±), (−) clausenamide on memory in water maze test

| Drugs | Doses (mg/kg) | Lalencies (sec) reaching platform | | |
| --- | --- | --- | --- | --- |
| | | Second day | $3^{rd}$ day | $4^{th}$ day |
| 0.9% Nacl | | 32.4 ± 29.2 | 25.8 ± 18.4 | 26.1 ± 38.4 |
| Piracetam | 500 | 32.2 ± 22.6 | 18.6 ± 9.9** | 16.7 ± 16.3** |
| (−) clausenamide | 10 | 28.7 ± 35.2 | 17.4 ± 10.9** | 12.1 ± 6.9** |

TAB 5-continued

Effects of piracetam, (±), (−) clausenamide on memory in water maze test

| Drugs | Doses (mg/kg) | Lalencies (sec) reaching platform | | |
|---|---|---|---|---|
| | | Second day | 3rd day | 4th day |
| (±) clausenamide | 10 | 35.8 ± 35.2 | 23.9 ± 22.6 | 17.1 ± 14.3 |
| | 50 | 36.6 ± 37.0 | 25.7 ± 13.8 | 14.6 ± 10.4** |

N = 10, X ± S.D.
**P < 0.05 vs 0.9% Nacl

TAB 6

Piracetam, (−), (±) clausenamide on memory impairment induced by anisodine in water maze test

| Drugs | Animals number | Doses (mg/kg) | Errors number |
|---|---|---|---|
| Anisodine | 10 | | 15.9 ± 11.3 |
| Piracetam | 9 | 500 | 23.5 ± 25.0 |
| (−)clausenamide | 10 | 10 | 9.4 ± 5.9** |
| (±)clausenamide | 8 | 10 | 16.6 ± 23.9 |
| | 8 | 100 | 9.11 ± 3.8** |

**P < 0.05 vs anisodine group

TAB 7

Effects of (−), (±) clausenamide on memory impairment induced by anisodine in step-through test

| Drugs | Doses (mg/kg) | Latencies (Sec) | Error number |
|---|---|---|---|
| 0.9% Nacl | | 152.1 ± 64.2 | 2.0 ± 3.8 |
| Anisodine | 10 | 35.8 ± 76.4** | 14.1 ± 8.9## |
| (−) clausenamide | 10 | 138.2 ± 86.7** | 6.7 ± 11.0* |
| | 50 | 140.6 ± 96.4** | 5.4 ± 4.1** |
| (±) clausenamide | 10 | 43.0 ± 65.8 | 11.3 ± 21.5 |
| | 50 | 79.9 ± 63.6 | 14.4 ± 12.3 |

N = 10
*P < 0.05
**P < 0.01 vs anisodine
## P < 0.01 vs 0.9% Nacl

EXAMPLE 23

Comparison of Improving Memorial Effects of (±) (−)Clausenamide

This invention used one trial avoidance task—step-down and step-through tests and water maze to compare the improving memorial effects of (±), (−) clausenamide.

The drugs were given orally once to animals before experiment in step-down and step-through tests. The water maze test lasted for 5 days in succession. The results were expressed as latency and errors number.

The results were shown in Tab.4 to Tab.7 All these results showed that the effective dosage for (−) clausenamide were 5,10,50 mg.kg$^{-1}$. The effective dose of piracetam was 500 mg.kg$^{-1}$. So the nootropic action of (−) clausenamide was 5–10 times and 50–100 times more potent than those of (±) clusenamide and piracetam.

EXAMPLE 24

Comparative Study on the Effects of (±) and (−) Clausenamide on LTP

Drugs or vehicle injection were delivered via cannula in the lateral cerebral ventricle at final concentration of $2 \times 10^{-6}$ mol/L. The population spike (PS) amplitude was employed as an indication of the level of excitation of the granular cell population in the dentate gyrus. To obtain this measurement, an evoked response was generated in the dentate gyrus granule cell layer by stimulating the pp at low freguency (0.033 Hz) with. single square wave pulses of 0.15 ms duration The LTP formation must accord the following creteria: The PS amplitude increased is over 30% and this high PS amplitude can persist for 40 min.

Results showed that 30–60 min after drug administration, (−)clusenamide increased PS amplitude by 48.5±81.2% and 38.9–63.4% in comparison with before drug administration and vehicle group, indicating that (−) clausenamide could increase basal synaptic transmission and induce LTP formation (see Tab 8).

(±) clausenamide at concentration of 2 $\mu$M to 10 $\mu$M showed inhibitory effect on PS amplitude. At time of 60 min following(±) clausenamide, the PS amplitude decreased by 44 and 55% compared with that of (−) clausenamide. This indicated that (±) clausenamide at dosage of increasing 5 times could not induce LTP, but inhibit basic synaptic transmission(FIG. 6)

TABLE 8

Effects of (−) clausenamide ((−) CLA) and (+) clausenamide ((+) CLA) on basal synaptic transmission in denate gyrus of hippocampus in anesthetized rats

| Groups | Before drug | After drug | | | | | | |
|---|---|---|---|---|---|---|---|---|
| | | 15' | PS % | 30' | PS % | 45' | PS % | 60' | PS % |
| Control | 103 ± 3 | 110 ± 9 | 6.7 | 108 ± 7 | 4.9 | 110 ± 10 | 6.7 | 112 ± 7 | 8.7 |
| (−) CLA | 101 ± 1 | 121 ± 9 | 19.8 | 150 ± 11 | 48.5 | 168 ± 25 | 66.3 | 183 ± 30 | 81.2 |
| PS % | −1.9 | 10.0 | | 38.9 | | 52.7 | | 63.4 | |
| (+) CLA | 101 ± 3 | 107 ± 8 | | 95 ± 9 | −5.9 | 88 ± 15 | −12.9 | 86 ± 18 | −14.9 |
| PS % | −1.9 | −2.7 | | −12.0 | | −20.0 | | −23.2 | |

EXAMPLE 25

Effect of Four Pairs Optically Active of "Clausenamide" on Induction of LTP in Hippocampal of Rat Method:

Adult male SD rats were anesthetized to maintain a surgical level. A stainless steel cannula-recording electrode was placed in DG (dentate gyrus) of hippocampus using a stereotaxic instrument. The combination of cannula-recording electrode was constructed by insulating the outside of the cannula, except at the tip and top. In the top noninsulated area, a stainless steel wire was wrapped around the cannula and connected to the amplifier via an amphenol connector. The four pairs optically active clausenamides shown in table 9 was delivered by I.C.V. Responses were evoked via direct stimulation of the performant path (PP) using a stainless steel bipolar stimulating electrode. Constant current stimulation provided by a stimulator was delivered to the stimulating electrode through a Stimulus Isolation Unit.

Stimulation was delivered until antidromic spikes resulting from PP and stimulation were observed in the dentate. The stimulating electrode was adjusted until a characteristic EPSP was observed under constant current. The evoked responses were amplified on a series alternating current preamplifier, using a microcomputer, and then stored for off-line analysis using DataWave software. The current intensity that elicited a 50% maximal response in each animal was determined and used for all subsequent stimulation. To measure treatment effects, responses were evoked once every 30 sec throughout the entire experiment, and population spike amplitude(PSA) were calculated.

TABLE 9

Effect of four pairs optically active of "Clausenamide" on induction of LTP in hippocampal of rat

| Treatment | PSA (%), means ± SD | | |
|---|---|---|---|
| | 15 min | 30 min | 60 min |
| (−) clausenamide | 131.8 ± 0.4 | 138.5 ± 8.9 | 158.1 ± 4.2 |
| (+) clausenamide | 90.6 ± 0.3 | 110.1 ± 13.1 | 106.4 ± 4.1 |
| (−) epiclausenamide | 97.8 ± 21.7 | 91.2 ± 22.5 | 117.3 ± 22.5 |
| (+) epiclausenamide | 136.0 ± 22.8 | 147.5 ± 15.0 | 207.8 ± 12.8 |
| (−) cisclausenamide | 126.2 ± 2.3 | 141.2 ± 8.6 | 205.4 ± 24.7 |
| (+) cisclausenamide | 87.3 ± 4.4 | 102.9 ± 5.9 | 122.5 ± 14.5 |
| (−) cisneoclausenamide | 94.1 ± 6.7 | 98.2 ± 6.6 | 94.9 |
| (+) cisneoclausenamide | 135.0 ± 12.9 | 150.9 ± 19.9 | 192.3 ± 22.4 |

EXAMPLE 26

Effects of Three Pairs Optically Active of "Clausenamide" on Colony-Form Frequency in Human Embryonic Neural Stem Cells 1. Method Human embryonic brain neural stem cells(NSC) were dissociated enzymatically with 0.05% trypsin-0.53 mM EDTA and cultured in the DMEM/F12 medium with N2 supplement (GIBCO), fibroblast growth factor-2 (20 ng/ml), epidermal growth factor (20 ng/ml) at 37° C. The media were changed once every week. The single cell suspension from neurosphere cells of NSC was dissociated by 0.1% trypsin. $2 \times 10^4$ cells were seeded in a well of a 96-well plate. After 24 hours, the dose at 1 µM of tested chemical was added in a well. 6 chemicals, (−)neoclausenamide(−), (+)neoclausenamide(+), (−)epineoclausenamide(−), (+)epineoclausenamide(+), (−)cisneoclausenamide(−) and (+)cisneoclausenamide(+), were detected. 4 wells were used each group. The media with tested chemical were changed once every week. The colonies of NSC were formed and counted under a microscopy at 3 weeks, 4 weeks and 6 weeks.

2. Results

The results from Tab. X showed that the frequency of colonies of NSC was not significantly difference between control group and each group of 6 chemicals at 3 weeks and 4 weeks. At 6 weeks, there were significantly difference between control group and the group of (+)neoclausenamide (+), (−)epineoclausenamide(−), and (−)cisneoclausenamide (−), but there were not any difference between the control group and each group of the three chemicals such as (−)neoclausenamide(−), (+)epineoclausenamide(+), and (+)cisneo-clausenamide(+). Furthermore, the frequencies of NSC colonies of (+)neoclausenamide(+), (−)epineoclausenamide(−), and (−)cisneoclausenamide(−) were greatly higher than those of (−)neoclau-senamide(+), (+)epineoclausenamide(+), and (+)cisneoclau-senamide(+).

In conclusion, the three new chemicals, (+)neoclausenamide(+) $II_2$. (−)epineoclausenamide(−) $II_3$ and (−)cisneoclausenamide(−) $II_6$, could induce the increase of human embryonic neural stem cells. They may have the effects of promoting proliferation of NSC.

TABLE 10

Effects of Three Pairs Optically active "Clausenamides" on Colony-form Frequency in Human Embryonic Neural Stem Cells

| No. | Group | N | Dose µM | 3 weeks Colonies Mean ± SD | 4 weeks Colonies Mean ± SD | 6 weeks Colonies Mean ± SD |
|---|---|---|---|---|---|---|
| | Control(DMSO) | 4 | 0 | 43.00 ± 4.97 | 30.33 ± 4.99 | 22.25 ± 4.86 |
| 1.1 | (−)neoclausenamide(−) $II_2$ | 4 | 1 | 53.00 ± 6.71 | 37.50 ± 4.15 | 24.5 ± 4.43 |
| 1.2 | (+)neoclausenamide(+) $II_2$ | 4 | 1 | 49.00 ± 8.86 | 39.75 ± 7.50 | 30.00 ± 4.40 * |
| 2.1 | (−)epineoclausenamide(−) $II_3$ | 4 | 1 | 58.00 ± 13.02 | 36.75 ± 7.59 | 32.50 ± 7.05 * |
| 2.2 | (+)epineoclausenamide(+) $II_3$ | 4 | 1 | 49.75 ± 10.26 | 38.50 ± 5.02 | 26.00 ± 2.94 |
| 3.1 | (−)cisneoclausenamide(−) $II_6$ | 4 | 1 | 49.50 ± 5.43 | 35.25 ± 7.46 | 33.50 ± 4.20 # |
| 3.2 | (+)cisneoclausenamide(+) $II_6$ | 4 | 1 | 47.00 ± 9.03 | 42.50 ± 10.01 | 24.00 ± 4.69 |

* $p < 0.05$(single tail T test);
$p < 0.05$(double tail T test)

What is claimed is:

1. An optically active chiral compound of Formula II,

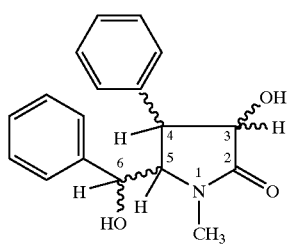

Formula II selected from the group consisting one of
3R4S5S6S (+) epiclausenamide,
3S4S5S6R (+) cisclausenamide, 3R4R5R6S (−) cisclausenamide,
3S4S5S6S (+) cisepiclausenamide, 3R4R5R6R (−) cisepiclausenamide,
3S4S5R6S (−) cisneoclausenamide, 3R4R5S6R (+) cisneoclausenamide,
3S4S5R6R (−) cisepineoclausenamide, and 3R4R5S6S (+) cisepineoclausenamide.

2. A pharmaceutical composition comprising an optically active compound as claimed in claim 1 and a pharmaceutically acceptable carrier or excipient.

3. A method for the treatment of a neurodegenerative disease comprising administering to a patient suffering from a neurodegenerative disease, an effective treatment amount of an optically active compound selected from the group consisting of

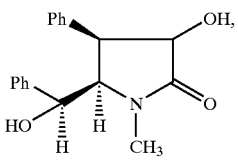

3S4R5S6R (−) neoclausenamide, 3R4S5R6S (+) neoclausenamide,
3S4R5S6S(−) epineoclausenamide, 3R4S5R6R (+) epioeoclausenamide,
3S4R5R6R (−) epiclausenamide, 3R4S5S6S (+) epiclausenamide,
3S4S5S6R (+) cisclausenamide, 3R4R5R6S (−) cisclausenamide,
3S4S5S6S (+) cisepiclausenamide, 3R4R5R6R (−) cisepiclausenamide,
3S4S5R6S (−) cisneoclausenamide, 3R4R5S6R (+) cisneoclausenamide,
3S4S5R6R (−) cisepineoclausenamide, and 3R4R5S6S (+) cisepineoclausenamide.

4. The method of claim 3, wherein the neurodegenerative disease is cerebral ischemia.

5. The method of claim 3, wherein the neurodegenerative disease is alzheimers disease.

6. The method of claim 3, wherein the neurodegenerative disease is vascular dementia.

* * * * *